US011926575B2

United States Patent
Takahashi

(10) Patent No.: US 11,926,575 B2
(45) Date of Patent: *Mar. 12, 2024

(54) COMPOUND, COMPOSITION, FILM, LAMINATE, AND DISPLAY DEVICE

(71) Applicant: Sumitomo Chemical Company, Limited, Tokyo (JP)

(72) Inventor: Keisuke Takahashi, Tsukuba (JP)

(73) Assignee: SUMITOMO CHEMICAL COMPANY, LIMITED, Tokyo (JP)

(*) Notice: Subject to any disclaimer, the term of this patent is extended or adjusted under 35 U.S.C. 154(b) by 82 days.

This patent is subject to a terminal disclaimer.

(21) Appl. No.: 17/628,980

(22) PCT Filed: Jun. 22, 2020

(86) PCT No.: PCT/JP2020/024358
§ 371 (c)(1),
(2) Date: Jan. 21, 2022

(87) PCT Pub. No.: WO2021/014855
PCT Pub. Date: Jan. 28, 2021

(65) Prior Publication Data
US 2022/0251029 A1 Aug. 11, 2022

(30) Foreign Application Priority Data

Jul. 23, 2019 (JP) ................................ 2019-135580
Oct. 4, 2019 (JP) ................................ 2019-184055

(51) Int. Cl.
| | | |
|---|---|---|
| C07C 245/08 | (2006.01) | |
| C07D 277/30 | (2006.01) | |
| C07D 277/66 | (2006.01) | |
| C07D 333/16 | (2006.01) | |
| C07D 333/60 | (2006.01) | |
| C07D 513/04 | (2006.01) | |
| C08F 220/34 | (2006.01) | |
| G02B 5/30 | (2006.01) | |

(52) U.S. Cl.
CPC .......... *C07C 245/08* (2013.01); *C07D 277/30* (2013.01); *C07D 277/66* (2013.01); *C07D 333/16* (2013.01); *C07D 333/60* (2013.01); *C07D 513/04* (2013.01); *C08F 220/346* (2020.02); *G02B 5/30* (2013.01)

(58) Field of Classification Search
CPC .................................................. C07C 245/08
See application file for complete search history.

(56) References Cited

U.S. PATENT DOCUMENTS

| | | | |
|---|---|---|---|
| 2007/0024970 A1 | 2/2007 | Lub et al. | |
| 2010/0267858 A1 | 10/2010 | Lub et al. | |
| 2015/0337203 A1 | 11/2015 | Hida et al. | |
| 2022/0251451 A1* | 8/2022 | Takahashi | ............... C08F 20/20 |

FOREIGN PATENT DOCUMENTS

| | | | |
|---|---|---|---|
| JP | H09087630 A | 3/1997 | |
| JP | H10287635 A | 10/1998 | |
| JP | H1112242 A | 1/1999 | |
| JP | 2007510946 A | 4/2007 | |
| JP | 2010026024 A | 2/2010 | |
| JP | 2011236178 A * | 11/2011 | ........... C07C 245/08 |
| JP | 2013037353 A | 2/2013 | |
| JP | 2013209367 A | 10/2013 | |
| JP | 2013227531 A | 11/2013 | |
| JP | 2016006502 A | 1/2016 | |
| JP | 2021017541 A | 2/2021 | |
| JP | 2021018405 A | 2/2021 | |
| WO | WO-2018/127245 A1 * | 12/2018 | ............. C09K 19/58 |

OTHER PUBLICATIONS

A machine generated English translation of WO 2018/127245 A1 to Yu et al., Jul. 12, 2018. (Year: 2018).*
Donovan et al., "All-Optical Control of Shape," Advanced Materials, vol. 31, pp. 1805750-1-1805750-7 (2019), published online Nov. 12, 2018.
Joly et al., "Light induced shifts of ferroelectric mesophase transitions," Liquid Crystals, vol. 26, No. 8, pp. 1251-1255 (1999).
Werth et al., "Twisted grain boundary phases in three new chiral azobenzene series," Liquid Crystals, vol. 17, No. 6, pp. 863-877 (1994).
Yang et al., "Synthesis and mesomorphic properties of fluoro-containing azobenzene liquid crystals," Liquid Crystals, vol. 28, No. 3, pp. 375-379 (2001).

* cited by examiner

*Primary Examiner* — Laura L Stockton
(74) *Attorney, Agent, or Firm* — Panitch Schwarze Belisario & Nadel LLP

(57) ABSTRACT

Provided is a compound represented by formula (1). In formula (1), $Ar^1$, $Ar^2$, and $Ar^3$ represent a 1,4-phenylene group or a divalent sulfur-containing aromatic heterocyclic group optionally having a substituent, and at least one of $Ar^1$ and $Ar^2$ has a fluorine atom as a substituent; n represents 1 or 2; $R^1$ represents a single bond or a group selected from the group consisting of —OC(=O)—, —C(=O)O—, —C≡C—, —CH=CH—, —CH=N—, and —N=CH—; $R^2$ represents an alkylamino group or an alkoxy group; $R^3$ represents a group selected from the group consisting of an alkanediyl group, an alkanediyloxy group, an alkanediyloxycarbonyl group, and an alkanediylcarbonyloxy group; and $R^4$ represents a polymerizable group or a hydrogen atom.

$$R^4—R^3—Ar^1—(—R^1—Ar^2—)_n-N=N-Ar^3—R^2 \quad (1)$$

9 Claims, No Drawings

COMPOUND, COMPOSITION, FILM, LAMINATE, AND DISPLAY DEVICE

CROSS-REFERENCE TO RELATED APPLICATIONS

This application is a Section 371 of International Application No. PCT/JP2020/024358, filed Jun. 22, 2020, which was published in the Japanese language on Jan. 28, 2021, under International Publication No. WO 2021/014855 A1, which claims priority under 35 U.S.C. § 119(b) to Japanese Application No. 2019-135580, filed Jul. 23, 2019, and Japanese Application No. 2019-184055, filed Oct. 4, 2019, the disclosure of each of which is incorporated herein by reference in its entirety.

TECHNICAL FIELD

The present invention relates to a compound, a composition, a film, a laminate, and a display device.

BACKGROUND ART

There is a continuous demand for reducing the thickness of a display such as an image display panel. There is also a demand for further reducing the thickness of a polarizing plate, a polarizer, or the like as one of constituent elements of the display. In response to such a demand, for example, a thin host-guest type polarizer including a polarizing film containing a polymerizable liquid crystal compound and a dichroic dye compound has been proposed (see, for example, Patent Documents 1 and 2).

PRIOR ART DOCUMENTS

Patent Documents

Patent Document 1: JP-A-2007-510946
Patent Document 2: JP-A-2013-37353

SUMMARY OF THE INVENTION

Problems to be Solved by the Invention

However, when ultraviolet (UV) exposure is used in a process of producing a polarizing film included in a polarizer, a dye compound may be denaturated, and therefore a processing process may be limited.

An object of the present invention is to provide a dye compound having high ultraviolet (UV) durability.

Means for Solving the Problems

The present invention provides the following [1] to [9].
[1] A compound represented by the following formula (1):

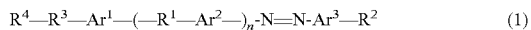   (1)

wherein $Ar^1$, $Ar^2$, and $Ar^3$ each independently represent a 1,4-phenylene group optionally having a substituent or a divalent sulfur-containing aromatic heterocyclic group optionally having a substituent, and at least one of $Ar^1$ and $Ar^2$ has a fluorine atom as a substituent; n represents an integer of 1 or 2. $R^1$ represents a single bond or at least one group selected from the group consisting of —OC(=O)—, —C(=O)O—, —C≡C—, —CH=CH—, —CH=N—, and —N=CH—; $R^2$ represents an alkylamino group optionally having a polymerizable group or an alkoxy group optionally having a polymerizable group. $R^3$ represents at least one group selected from the group consisting of an alkanediyl group having 4 to 20 carbon atoms, an alkanediyloxy group having 2 to 20 carbon atoms, an alkanediyloxycarbonyl group having 2 to 20 carbon atoms, and an alkanediylcarbonyloxy group having 2 to 20 carbon atoms; $R^4$ represents a polymerizable group or a hydrogen atom. when n is 2, two $R^1$s may be the same as or different from each other, and two $Ar^2$s may be the same as or different from each other.
[2] The compound according to [1], wherein either one of $Ar^1$ and $Ar^2$ has one or two fluorine atoms as a substituent in the formula (1).
[3] The compound according to [1] or [2], wherein $R^1$ is a single bond in the formula (1).
[4] The compound according to any one of [1] to [3], wherein n is an integer of 1 in the formula (1).
[5] The compound according to any one of [1] to [4], wherein the polymerizable group is a radically polymerizable group.
[6] A composition comprising the compound according to any one of [1] to [5].
[7] A film comprising the compound according to any one of [1] to [5] as a forming material.
[8] A laminate comprising the film according to [7].
[9] A display device comprising the film according to [7].

Effect of the Invention

The present invention can provide a dye compound having high ultraviolet durability.

MODE FOR CARRYING OUT THE INVENTION

In the present specification, the term "step" includes not only an independent step but also a step that cannot be clearly distinguished from other steps as long as an intended purpose of the step is achieved. In addition, when a plurality of substances corresponding to each component is present in a composition, the content of each component in the composition means the total amount of the plurality of substances present in the composition unless otherwise specified. Hereinafter, an embodiment of the present invention will be described in detail. Note that the scope of the present invention is not limited to the embodiment described here, and various modifications can be made without departing from the gist of the present invention.

<Compound>

A compound according to the present embodiment is a compound that can be used as a dye and has a structure represented by the following formula (1).

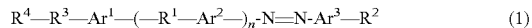   (1)

In formula (1), n is an integer of 1 or 2, and n is preferably 1. The geometric isomerism of the azo group in formula (1) may be either cis or trans, but is preferably trans.

$Ar^1$, $Ar^2$, and $Ar^3$ in formula (1) each independently represent a 1,4-phenylene group optionally having a substituent or a divalent sulfur-containing aromatic heterocyclic group optionally having a substituent.

Examples of the substituent in $Ar^1$, $Ar^2$, and $Ar^3$ include an alkyl group having 1 to 10 carbon atoms, such as a methyl group, an ethyl group, or a butyl group; an alkoxy group having 1 to 10 carbon atoms, such as a methoxy group, an ethoxy group, or a butoxy group; a fluorinated alkyl group having 1 to 10 carbon atoms, such as a trifluoromethyl group; a cyano group; a nitro group; a halogen atom such as a chlorine atom or a fluorine atom; and a substituted or unsubstituted amino group such as an amino group, a diethylamino group, or a pyrrolidino group. Here, the substituted amino group means an amino group having one or two alkyl groups each having 1 to 10 carbon atoms on a nitrogen atom, or an amino group in which two alkyl groups on a nitrogen atom are bonded to each other to form an alkanediyl group having 2 to 8 carbon atoms. In addition, the unsubstituted amino group is —NH$_2$. Examples of the alkyl group having 1 to 10 carbon atoms include a methyl group, an ethyl group, and a hexyl group. Examples of the alkanediyl group having 2 to 8 carbon atoms include an ethylene group, a propane-1,3-diyl group, a butane-1,3-diyl group, a butane-1,4-diyl group, a pentane-1,5-diyl group, a hexane-1,6-diyl group, a heptane-1,7-diyl group, and an octane-1,8-diyl group.

In the compound according to the present embodiment, at least one of $Ar^1$ and $Ar^2$ has a fluorine atom as a substituent. The total number of fluorine atoms included in $Ar^1$ and $Ar^2$ is preferably 1 or more and 4 or less, more preferably 1 or 2, and still more preferably 1. Either one of $Ar^1$ and $Ar^2$ preferably has a fluorine atom as a substituent. Either one of $Ar^1$ and $Ar^2$ preferably has one or more and four or less fluorine atoms, more preferably has one or two fluorine atoms, and still more preferably has one fluorine atom.

The compound represented by formula (1) can exhibit excellent ultraviolet durability because at least one of $Ar^1$ and $Ar^2$ has a fluorine atom as a substituent. As a result, in a process for producing a polarizing plate including a film containing the compound represented by formula (1) as a forming material, a decrease in the characteristics of a polarizing plate to be produced is suppressed even when ultraviolet exposure is used, and the range of options of the production process can be widened. Here, the ultraviolet durability of the dye compound can be evaluated by, for example, an absorbance retention ratio of a film formed from the dye compound before and after ultraviolet irradiation. For example, the absorbance retention ratio of the dye compound before and after UV irradiation of 3000 mJ/cm$^2$ is 80% or more, 85% or more, or 90% or more.

As a substituent other than the fluorine atom included in $Ar^1$, $Ar^2$, and $Ar^3$, a methyl group or a methoxy group is preferable. This makes it easier for the compound represented by formula (1) to be included in a highly ordered liquid crystal structure such as a smectic liquid crystal. In addition, the number of substituents other than a fluorine atom included in $Ar^1$, $Ar^2$, and $Ar^3$ is preferably one or two. This makes it easier for the compound represented by formula (1) to be included in a highly ordered liquid crystal structure such as a smectic liquid crystal.

In addition, when n is 1, at least two of $Ar^1$, $Ar^2$, and $Ar^3$ are preferably 1,4-phenylene groups in that the compound represented by formula (1) has both convenience in molecular synthesis and high performance.

Examples of the divalent sulfur-containing aromatic heterocyclic group in $Ar^1$, $Ar^2$, and $Ar^3$ include a group formed by removing two hydrogen atoms from a sulfur-containing aromatic heterocyclic compound selected from the group consisting of thiophene, benzothiophene, dibenzothiophene, benzodithiophene, thienofuran, thienothiophene, furothiazole, thienothiazole, and benzothiazole.

When the compound according to the present embodiment has a structure in which a divalent sulfur-containing aromatic heterocyclic group and a 1,4-phenylene group are directly bonded to each other, a dichroic ratio of a film containing the compound is improved. Furthermore, the film containing the compound has a high dichroic ratio retention ratio when a dichroic ratio is compared between before UV exposure and after UV exposure.

$R^1$ represents a single bond or at least one linking group selected from the group consisting of —OC(=O)—, —C(=O)O—, —C≡C—, —CH=CH—, —CH=N—, and —NH=C—. When there is a plurality of $R^1$s, $R^1$s may be the same as or different from each other.

$R^1$ is preferably a single bond, —OC(=O)—, or —C(=O)O—, and more preferably a single bond.

$R^2$ represents an alkylamino group optionally having a polymerizable group or an alkoxy group optionally having a polymerizable group. As the polymerizable group in $R^2$, a radically polymerizable group is preferable, and examples of the radically polymerizable group include a radically polymerizable group such as a (meth)acrylate group ((meth)acryloyloxy group) or a styryl group (vinylphenyl group). Among these groups, a (meth)acrylate group is preferable. When $R^2$ has a polymerizable group, the number of the polymerizable groups is, for example, 1 or 2, and preferably 1.

Examples of the alkylamino group in $R^2$ include an amino group having one or two alkyl groups each having 1 to 10 carbon atoms on a nitrogen atom, and a cyclic amino group in which two alkyl groups on a nitrogen atom are bonded to each other to form an alkanediyl group having 2 to 8 carbon atoms. Specific examples of the alkylamino group in $R^2$ include a methylamino group, an ethylamino group, a dimethylamino group, a diethylamino group, a dipropylamino group, a methylethylamino group, a methylhexylamino group, a pyrrolidino group, a piperidino group, and a morpholino group. The alkylamino group in $R^2$ is preferably at least one selected from the group consisting of a dimethylamino group, a diethylamino group, a dipropylamino group, a methylethylamino group, and a methylhexylamino group.

Examples of the alkoxy group in $R^2$ include an alkoxy group having 1 to 10 carbon atoms. Specific examples of the alkoxy group in $R^2$ include a methoxy group, an ethoxy group, a propyloxy group, a butyloxy group, a pentyloxy group, a hexyloxy group, a cyclopentyloxy group, and a cyclohexyloxy group. The alkoxy group in $R^2$ is preferably at least one selected from the group consisting of an ethoxy group, a propyloxy group, and the like.

$R^3$ in formula (1) represents at least one divalent group selected from the group consisting of an alkanediyl group having 4 to 20 carbon atoms, an alkanediyloxy group having 2 to 20 carbon atoms, an alkanediyloxycarbonyl group having 2 to 20 carbon atoms, and an alkanediylcarbonyloxy group having 2 to 20 carbon atoms.

Examples of the alkanediyl group having 4 to 20 carbon atoms include an alkanediyl group formed by removing one hydrogen atom from an unsubstituted (not having a substituent) linear or branched alkyl group having 4 to 20 carbon atoms, such as a n-butyl group, an isobutyl group, a tert-butyl group, a n-pentyl group, an isopentyl group, a neopentyl group, a n-hexyl group, a n-heptyl group, a n-octyl group, a n-nonyl group, or a n-decyl group. The number of carbon atoms in the alkanediyl group is preferably 4 to 16, and more preferably 4 to 12.

One or more hydrogen atoms constituting the alkyl group having 4 to 20 carbon atoms may be substituted with a halogen atom (for example, a fluorine atom), a hydroxy group, an amino group, or a substituted amino group. Here, examples of the substituted amino group include an amino group substituted with one or two alkyl groups each having 1 to 20 carbon atoms, such as an N-methylamino group, an N-ethylamino group, an N,N-dimethylamino group, or an N,N-diethylamino group. Examples of the alkyl group in which one or more hydrogen atoms are substituted with a halogen atom, a hydroxy group, an amino group, or the like include: a haloalkyl group having 4 to 20 carbon atoms, such as a fluorobutyl group or an octafluorobutyl group; a hydroxyalkyl group having 4 to 20 carbon atoms, such as a hydroxybutyl group, a hydroxypentyl group, or a hydroxyhexyl group; and an alkyl group having 4 to 20 carbon atoms and having an unsubstituted amino group or a substituted amino group, such as an aminobutyl group or a 2-(N,N-dimethylamino) butyl group.

—O— or —NR*— may be inserted between carbon atoms constituting the alkyl group. Here, R* represents a hydrogen atom or an alkyl group having 1 to 6 carbon atoms, preferably 1 to 4 carbon atoms, and examples of the alkyl group having 1 to 6 carbon atoms include a methyl group, an ethyl group, a butyl group, and a hexyl group. Examples of the alkyl group having —O— or —NR*— inserted between carbon atoms include a 2-ethoxyethyl group, a 2-(2-ethoxyethoxy) ethyl group, and a 2-[2-(ethylamino) ethyl) amino] ethyl group.

Examples of the alkanediyloxy group having 2 to 20 carbon atoms include an alkanediyloxy group formed by removing one hydrogen atom from an unsubstituted linear or branched alkoxy group having 2 to 20 carbon atoms, such as an ethoxy group, a n-propoxy group, an isopropyloxy group, a n-butoxy group, an isobutyloxy group, a tert-butoxy group, a n-pentyloxy group, an isopentyloxy group, a neopentyloxy group, a n-hexyloxy group, a n-heptyloxy group, a n-octyloxy group, a n-nonyloxy group, or a n-decyloxy group. The number of carbon atoms in the alkanediyloxy group is preferably 2 to 16, and more preferably 2 to 12.

One or more hydrogen atoms constituting the alkoxy group having 2 to 20 carbon atoms may be substituted with a halogen atom (for example, a fluorine atom), a hydroxy group, an amino group, or a substituent amino group. The substituent amino group is similar to that described above. Examples of the alkoxy group in which one or more hydrogen atoms are substituted with a halogen atom, hydroxy, an amino group, or the like include: a haloalkoxy group having 2 to 20 carbon atom, such as a tetrafluoroethoxy group or an octafluorobutoxy group; a hydroxyalkoxy group having 2 to 20 carbon atoms, such as a 2-hydroxyethoxy group; and an alkoxy group having 2 to 20 carbon atoms and having an unsubstituted amino group or a substituent amino group, such as an aminoethoxy group or a 2-(N,N-dimethylamino) ethoxy group.

—O— or —NR*— may be inserted between carbon atoms constituting the alkoxy group. Examples of the alkoxy group in which —O— or —NR*— is inserted between carbon atoms include a methoxymethoxy group, a 2-ethoxyethoxy group, and a 2-(2-ethoxyethoxy) group. Note that R* is as described above.

Examples of the alkanediyloxycarbonyl group having 2 to 20 carbon atoms include an alkanediyloxycarbonyl group formed by removing one hydrogen atom from an unsubstituted alkoxycarbonyl group having 2 to 20 carbon atoms, such as a methoxycarbonyl group, an ethoxycarbonyl group, a n-propoxycarbonyl group, an isopropoxycarbonyl group, a n-butoxycarbonyl group, an isobutoxycarbonyl group, a tert-butoxycarbonyl group, a n-pentyloxycarbonyl group, an isopentyloxycarbonyl group, a neopentyloxycarbonyl group, a n-hexyloxycarbonyl group, a n-heptyloxycarbonyl group, a n-octyloxycarbonyl group, a n-nonyloxycarbonyl group, or a n-decyloxycarbonyl group. The number of carbon atoms in the alkanediyl moiety of the alkanediyloxycarbonyl group is preferably 1 to 16, and more preferably 1 to 12.

One or more hydrogen atoms constituting the alkoxycarbonyl group having 2 to 20 carbon atoms may be substituted with a halogen atom (for example, a fluorine atom), a hydroxy group, an amino group, or an amino group having a substituent. The amino group having a substituent is similar to that described above. Examples of the alkoxycarbonyl group in which one or more hydrogen atoms are substituted with a halogen atom, a hydroxy group, an amino group, or the like include a haloalkoxycarbonyl group having 2 to 20 carbon atoms, such as a fluoroethoxycarbonyl group, a trifluoroethoxycarbonyl group, a tetrafluoroethoxycarbonyl group, or an octafluorobutoxycarbonyl group.

Examples of the alkanediylcarbonyloxy group having 2 to 20 carbon atoms include an alkanediylcarbonyloxy group formed by removing one hydrogen atom from an unsubstituted alkanoyloxy group having 2 to 20 carbon atoms, such as an acetyloxy group, an ethylcarbonyloxy group, a n-propylcarbonyloxy group, an isopropylcarbonyloxy group, a n-butylcarbonyloxy group, an isobutylcarbonyloxy group, a tert-butylcarbonyloxy group, a n-pentylcarbonyloxy group, an isopentylcarbonyloxy group, a neopentylcarbonyloxy group, a n-hexylcarbonyloxy group, a n-heptylcarbonyloxy group, a n-octylcarbonyloxy group, a n-nonylcarbonyloxy group, or a n-decylcarbonyloxy group. The number of carbon atoms in the alkanediyl moiety of the alkanediylcarbonyloxy group is preferably 1 to 16, and more preferably 1 to 12.

One or more hydrogen atoms constituting the alkanoyloxy group having 2 to 20 carbon atoms may be substituted with a halogen atom (for example, a fluorine atom), a hydroxy group, an amino group, or an amino group having a substituent. The amino group having a substituent is similar to that described above. Examples of the alkanoyloxy group in which one or more hydrogen atoms are substituted with a halogen atom, a hydroxy group, or the like include a haloacyloxy group having 2 to 20 carbon atoms, such as a tetrafluoroethylcarbonyloxy group or an octafluorobutylcarbonyloxy group.

$R^4$ in formula (1) represents a polymerizable group or a hydrogen atom. As the polymerizable group in $R^4$, a radically polymerizable group is preferable, and examples of the radically polymerizable group include a (meth)acrylate group and a styryl group. Among these groups, a (meth)acrylate group is preferable.

The compound represented by formula (1) is preferably a dichroic dye. The dichroic dye refers to a dye having a property that absorbance of a molecule in a major axis direction is different from absorbance of the molecule in a minor axis direction. The dichroic dye preferably has a characteristic of absorbing visible light, more preferably has an absorption maximum wavelength ($\lambda_{MAX}$) in a range of 380 nm or more and 680 nm or less, and still more preferably has an absorption maximum wavelength ($\lambda_{MAX}$) in a range of 420 nm or more and 520 nm or less.

Specific examples of the compound represented by formula (1) include the following compounds represented by formula (2-2) to formula (2-102), but the present invention is not limited thereto.

[Chemical formula 1]
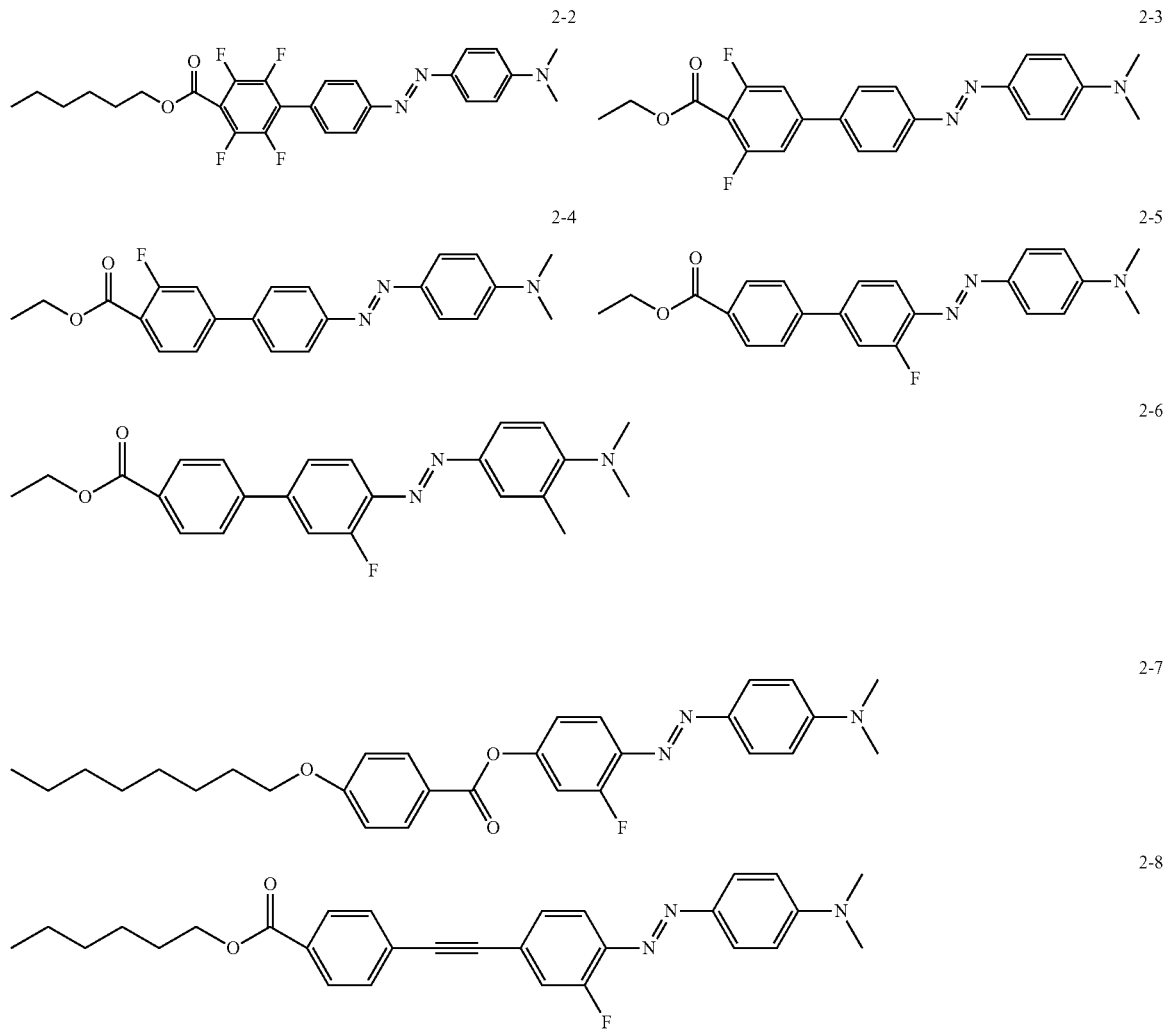
[Chemical formula 2]
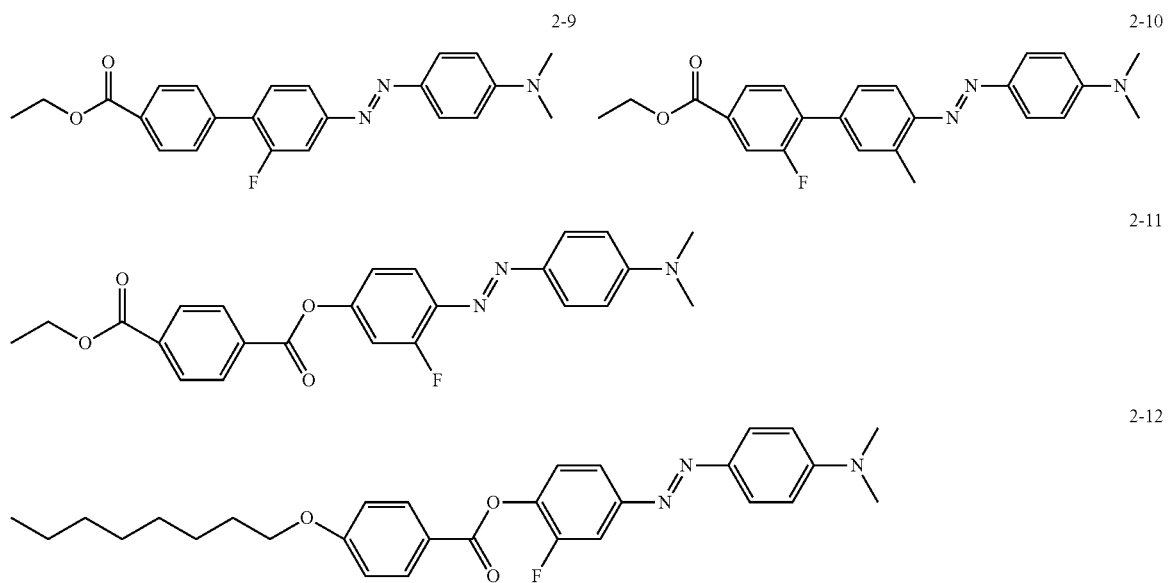

-continued
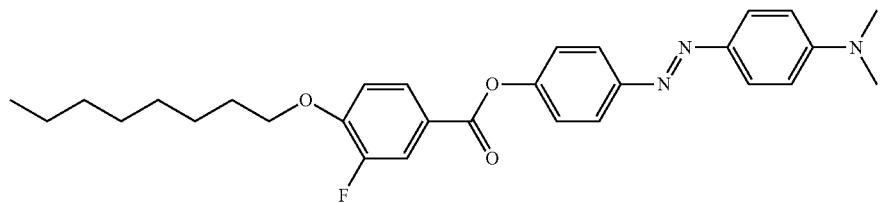
2-13
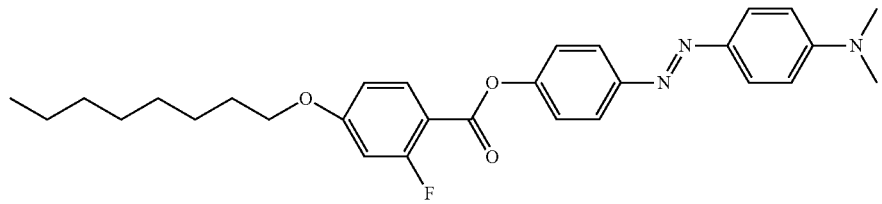
2-14
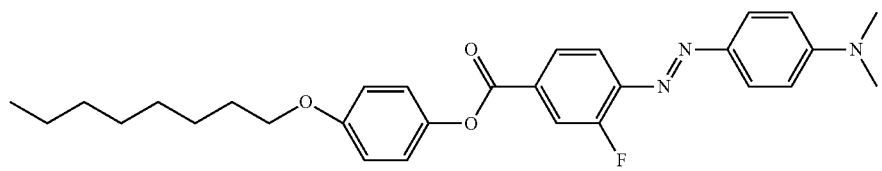
2-15
[Chemical formula 3]
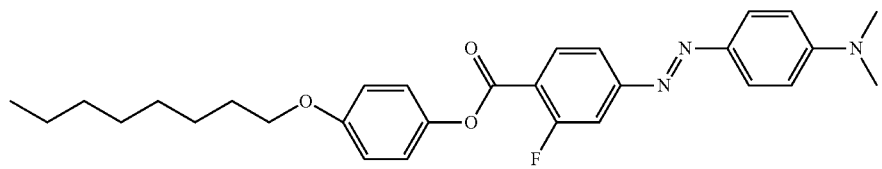
2-16
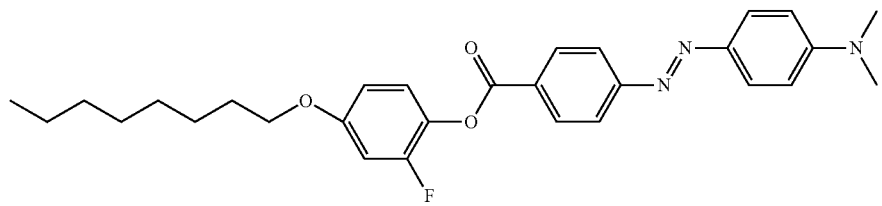
2-17
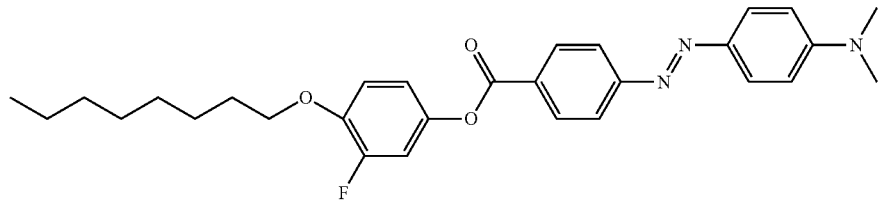
2-18
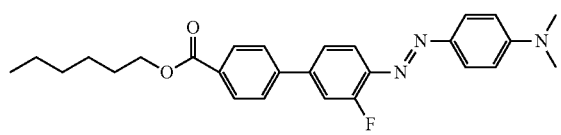
2-19
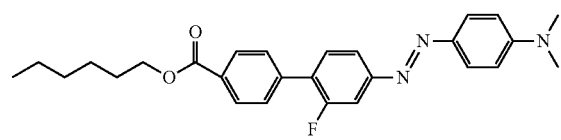
2-20
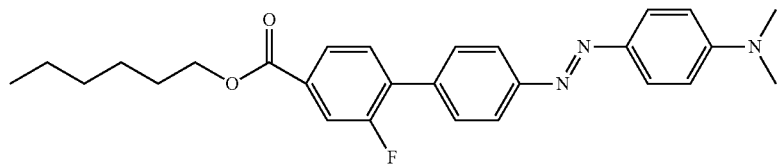
2-21

[Chemical formula 4]
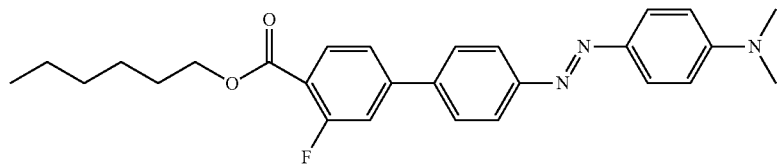
2-22
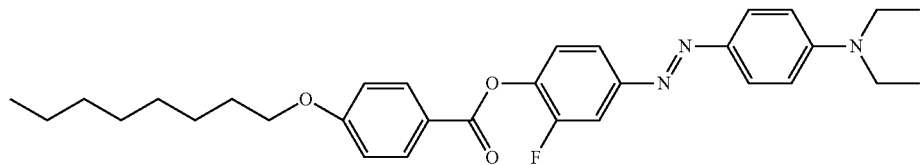
2-23
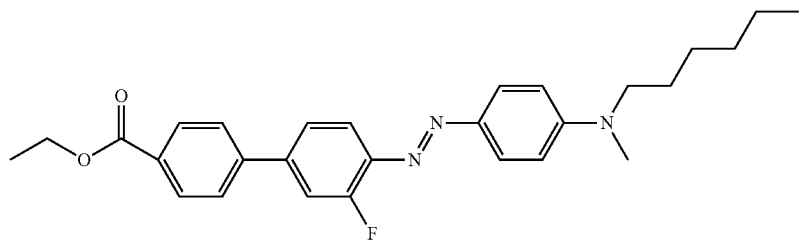
2-24
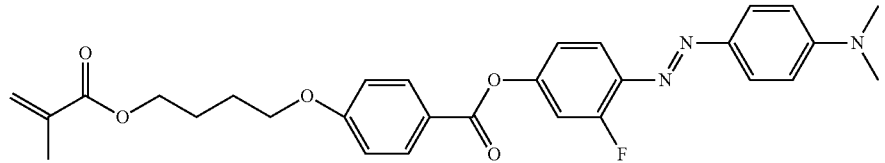
2-25
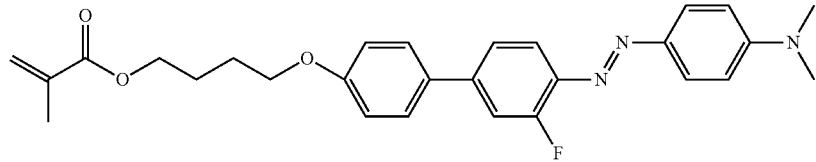
2-26
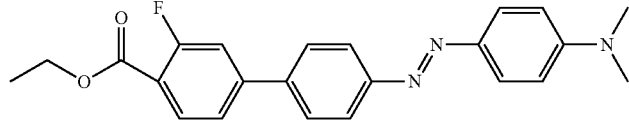
2-27
[Chemical formula 5]
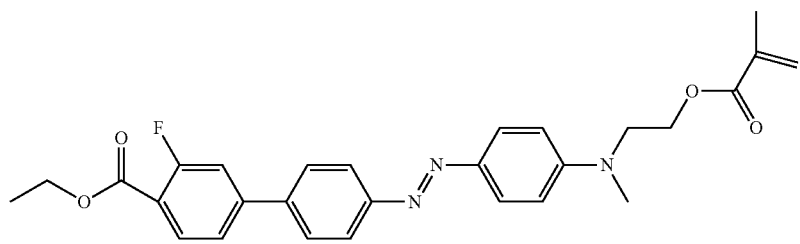
2-28

-continued
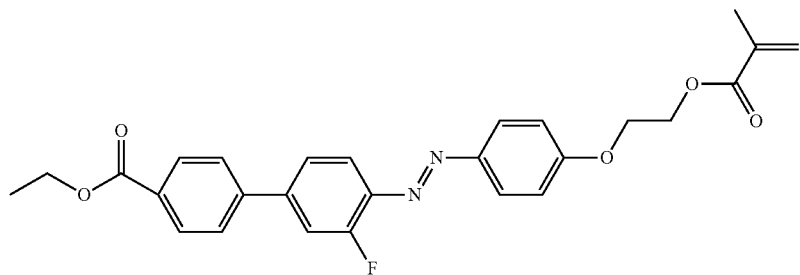
2-29
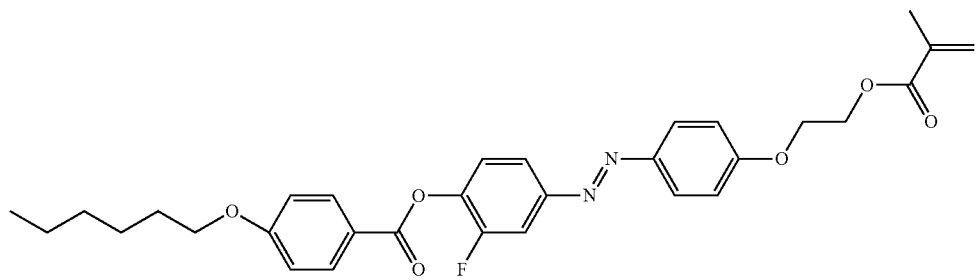
2-30
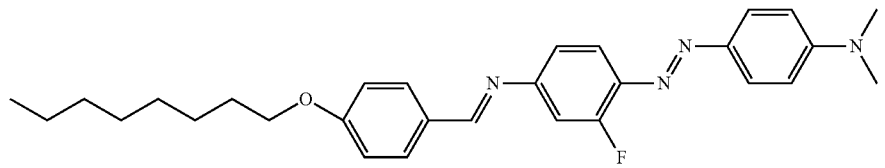
2-31
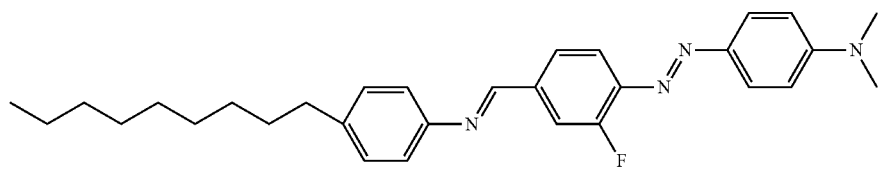
2-32
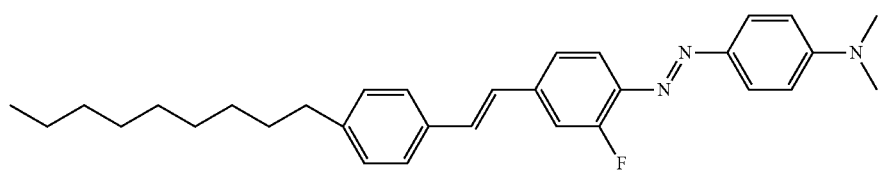
2-33
[Chemical formula 6]
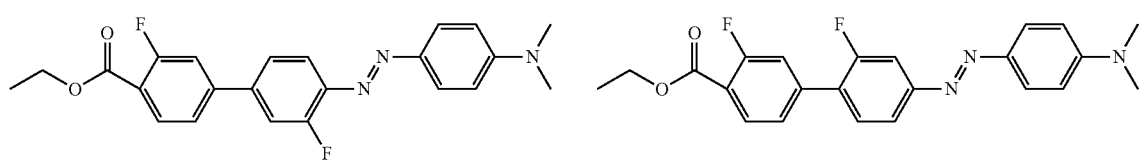
2-34 2-35
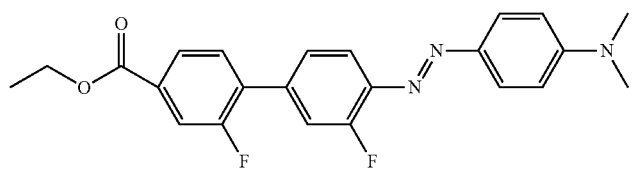
2-36

[Chemical formula 7]
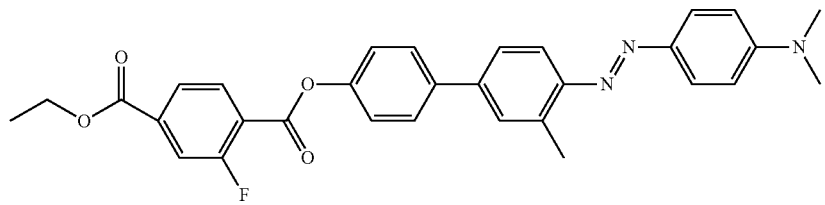
2-37
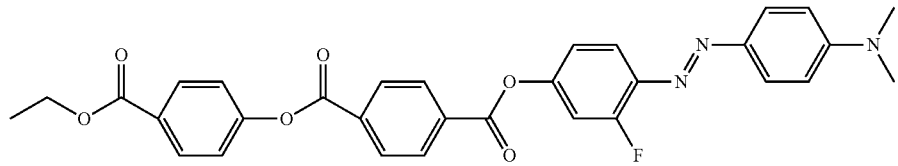
2-38
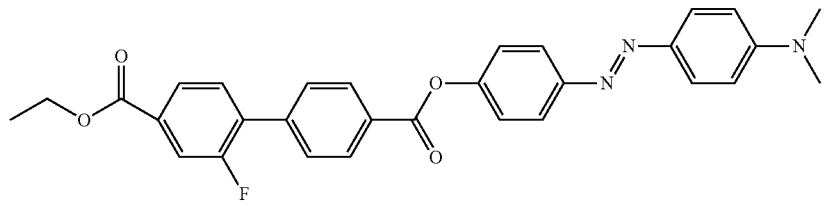
2-39
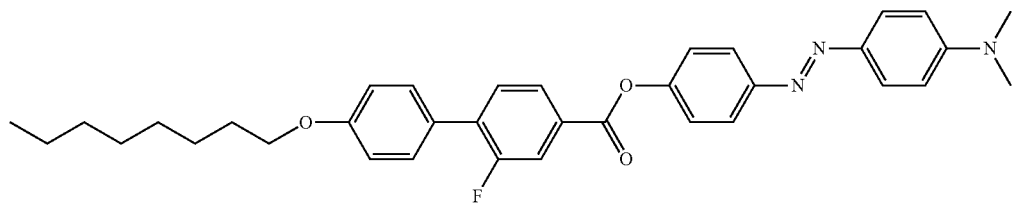
2-40
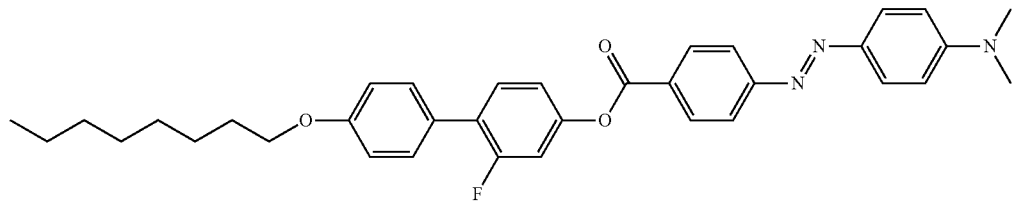
2-41
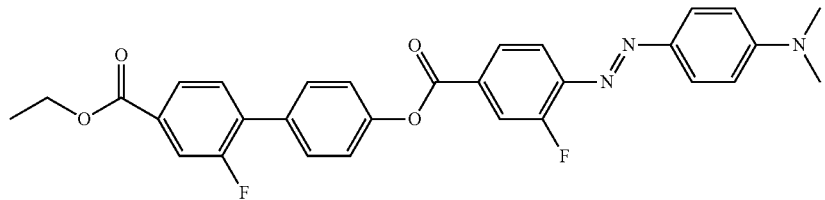
2-42
[Chemical formula 8]
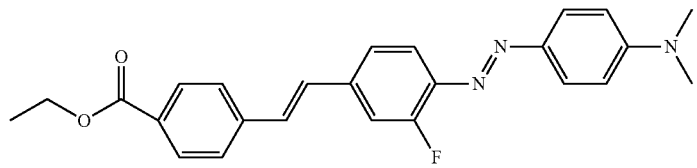
2-43

-continued
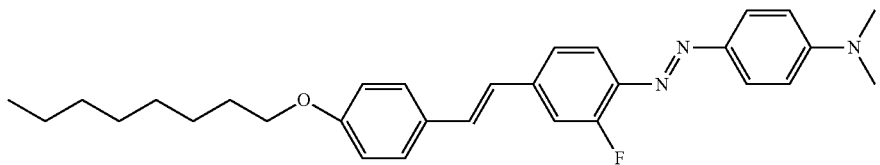
2-44
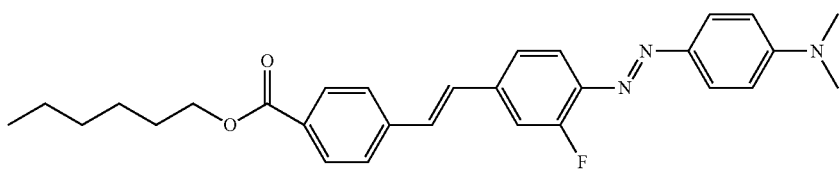
2-45
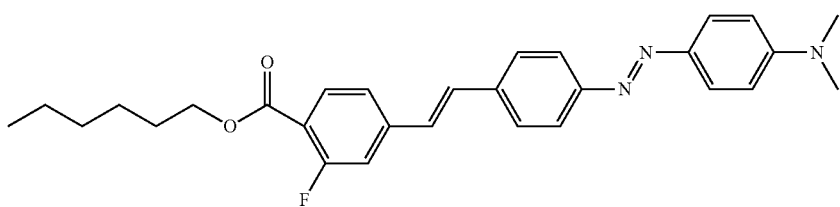
2-46
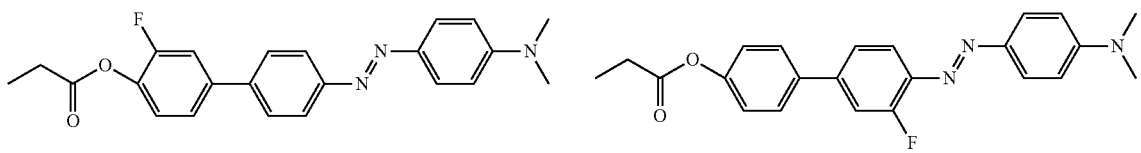
2-47    2-48
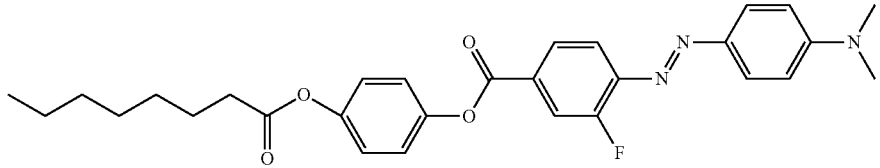
2-49
[Chemical formula 9]
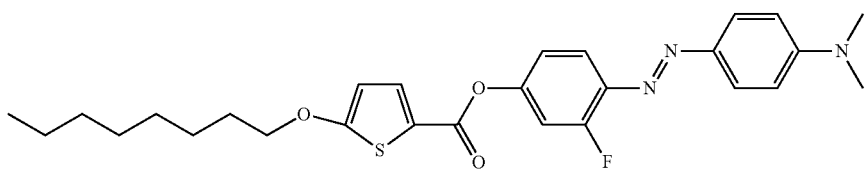
2-50
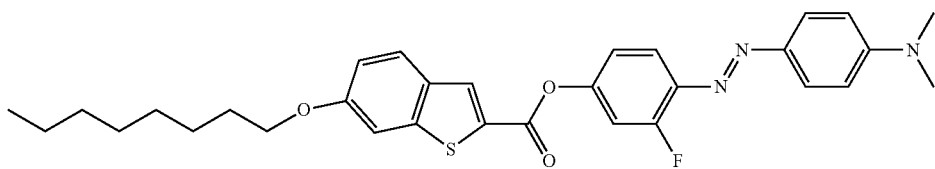
2-51
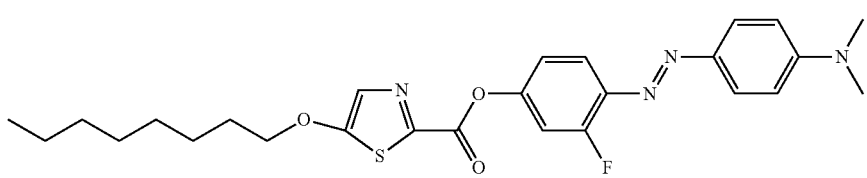
2-52

-continued
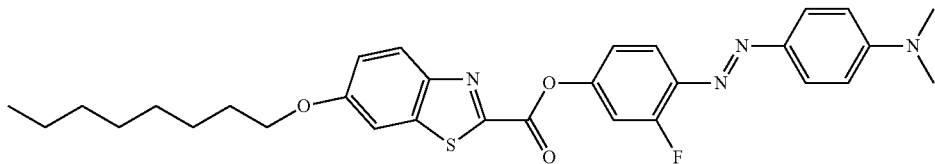
2-53
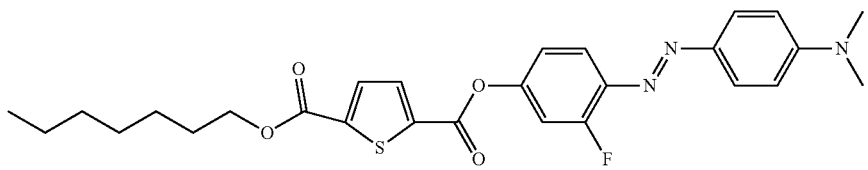
2-54
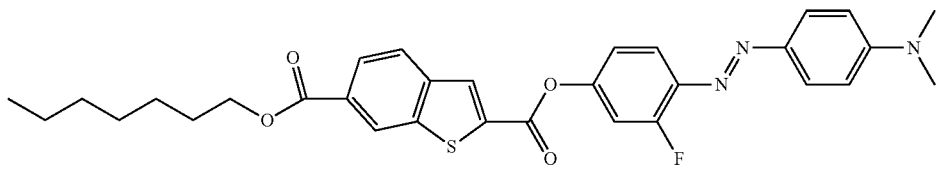
2-55
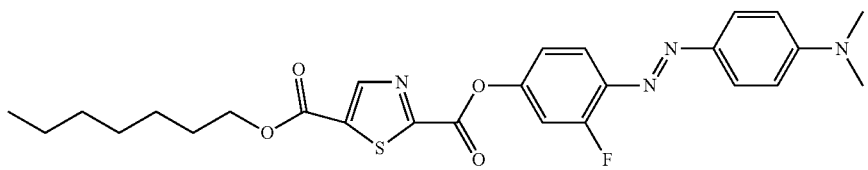
2-56
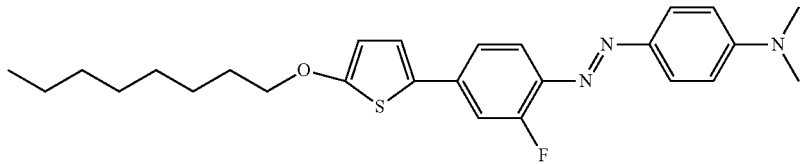
2-57
[Chemical formula 10]
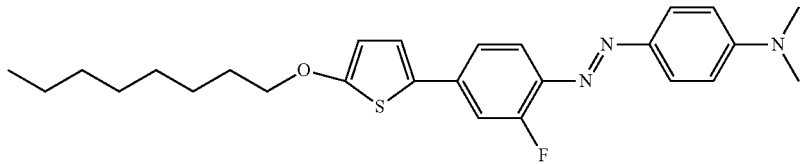
2-58
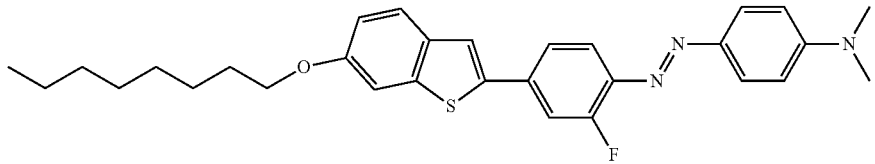
2-59
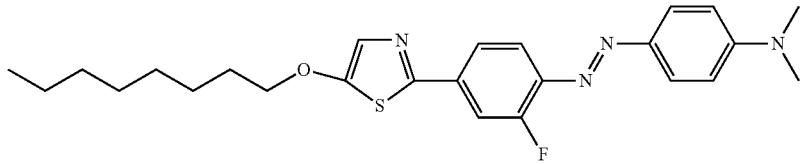
2-60
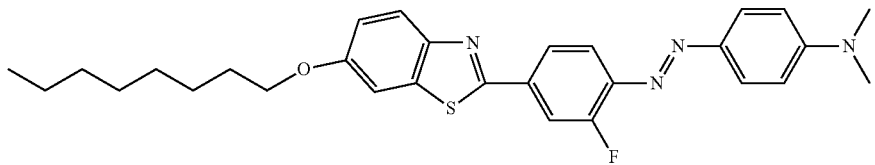
2-61

2-62
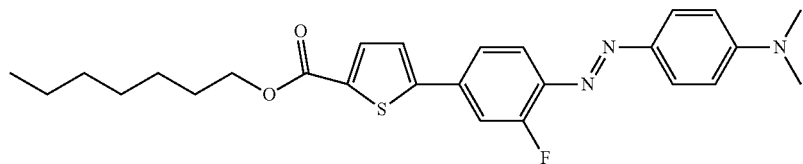
2-63
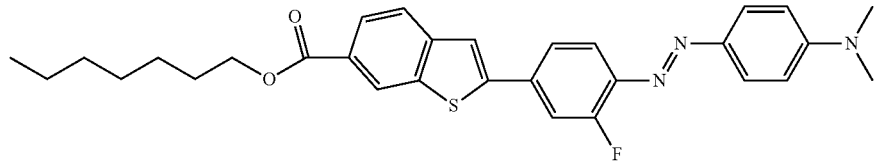
2-64
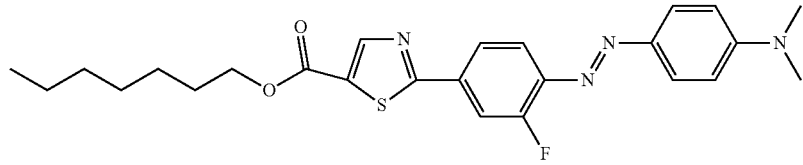
2-65
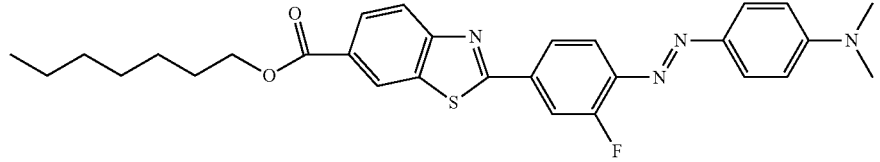
[Chemical formula 11]
2-66
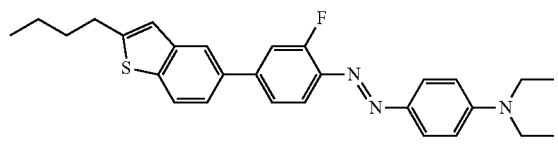
2-67
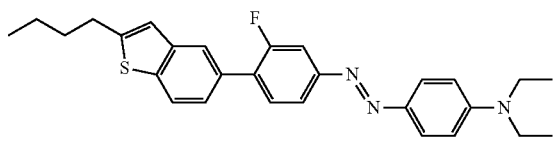
2-68
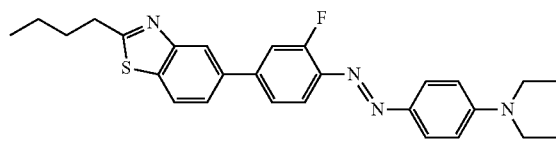
2-69
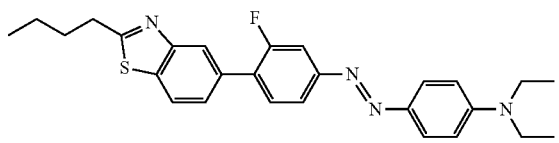
[Chemical formula 12]
2-70
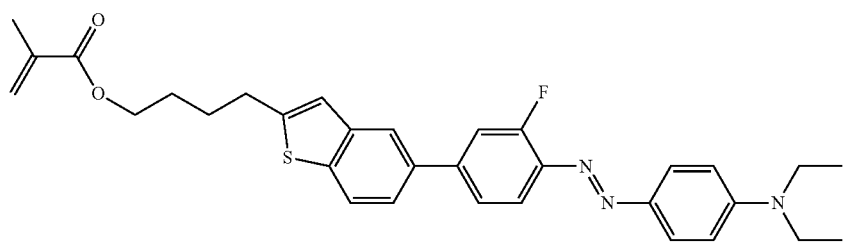
2-71
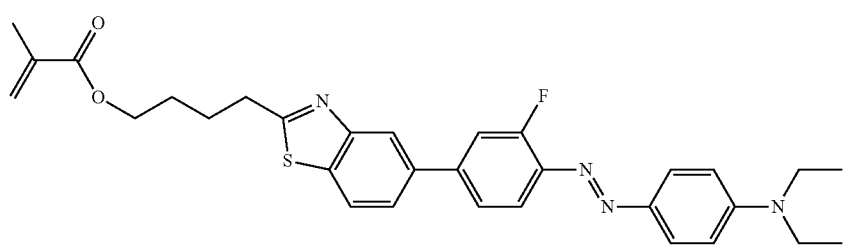

-continued
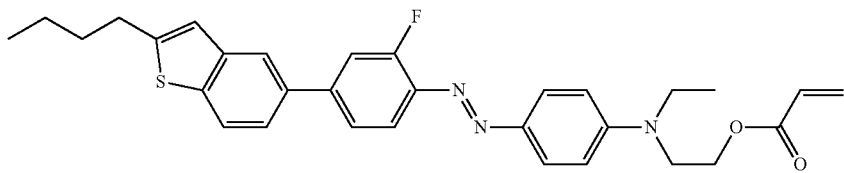
2-72
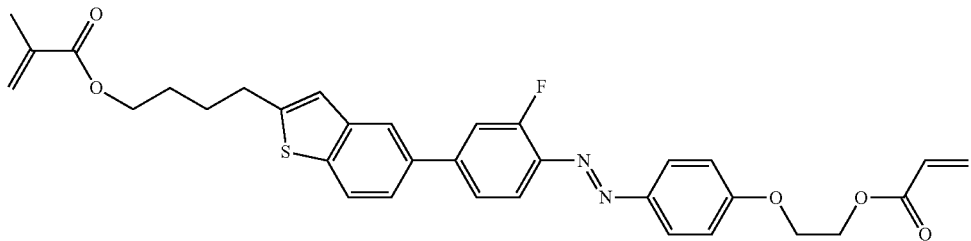
2-73
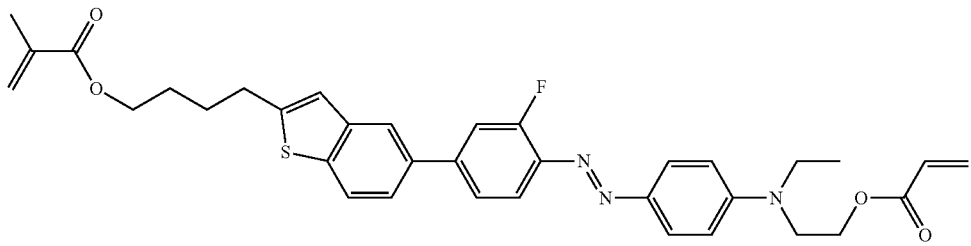
2-74
[Chemical formula 13]
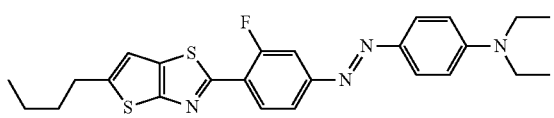
2-75
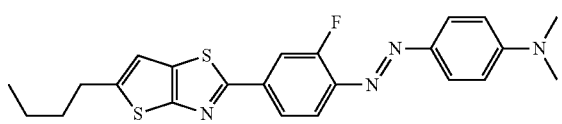
2-76
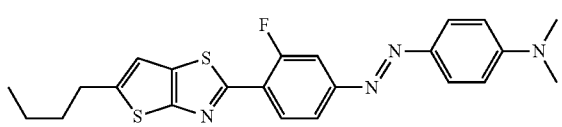
2-77
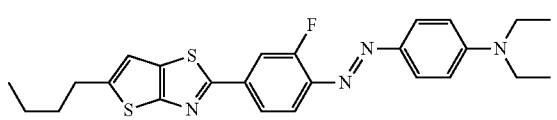
2-78
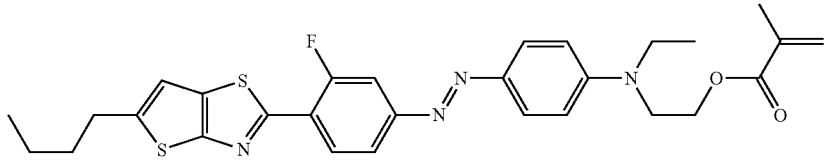
2-79
[Chemical formula 14]
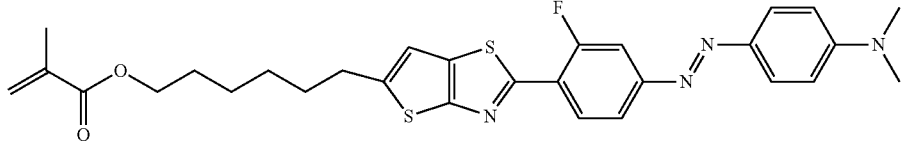
2-80
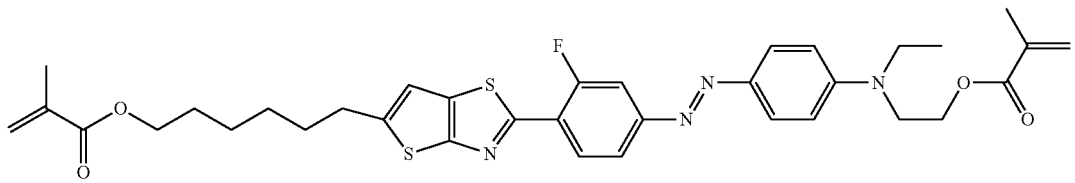
2-81

-continued
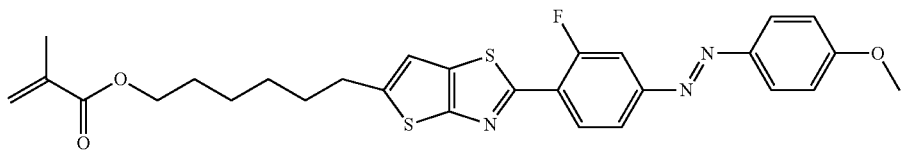
2-82
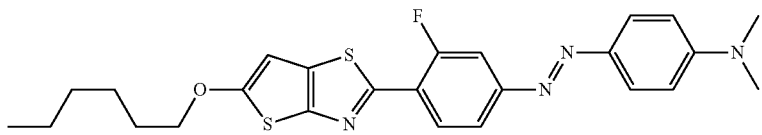
2-83
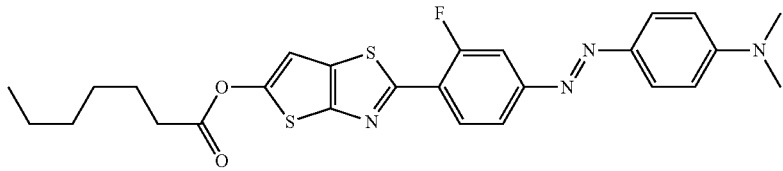
2-84
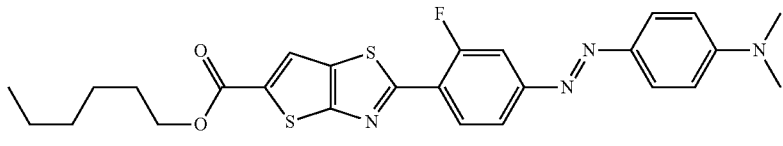
2-85
[Chemical formula 15]
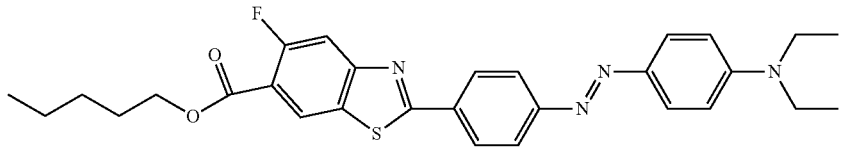
2-86
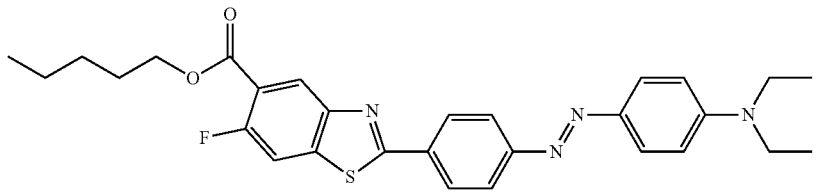
2-87
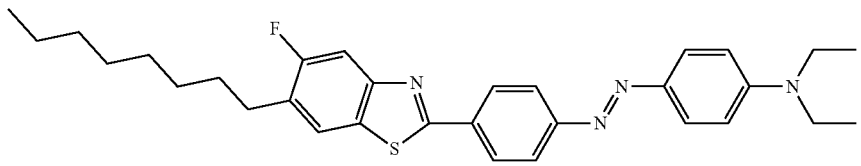
2-88
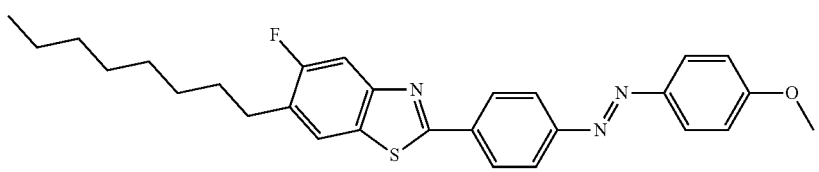
2-89
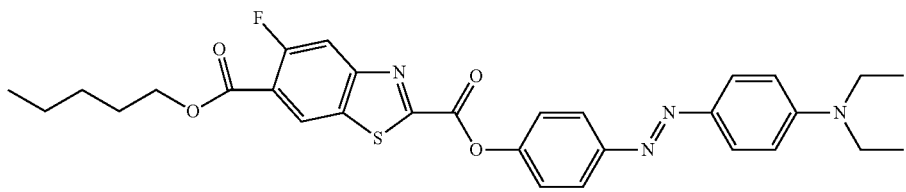
2-90

-continued
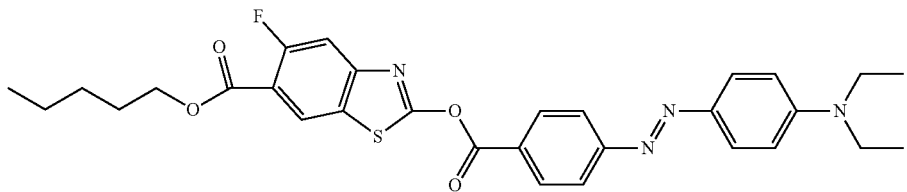
2-91
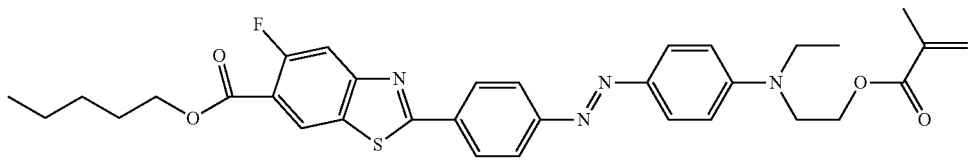
2-92
[Chemical formual 16]
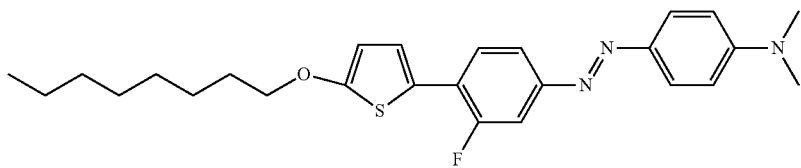
2-93
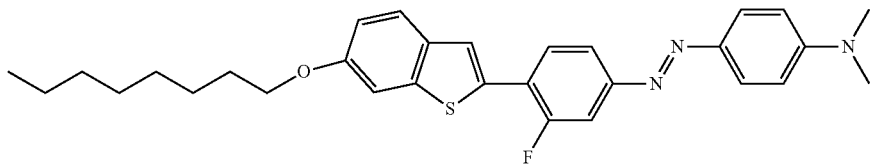
2-94
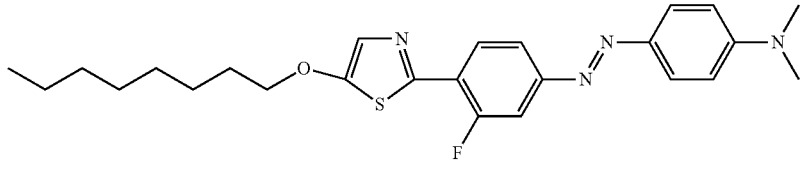
2-95
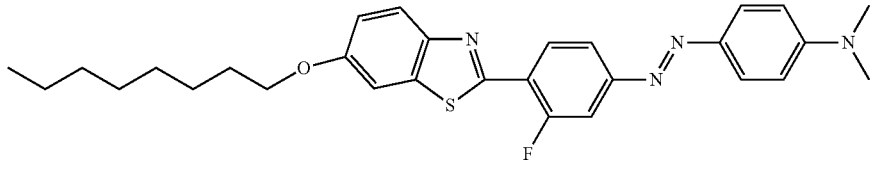
2-96
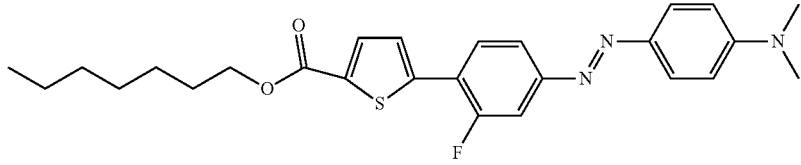
2-97
[Chemical formula 17]
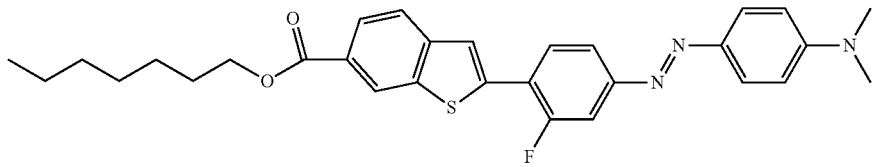
2-98

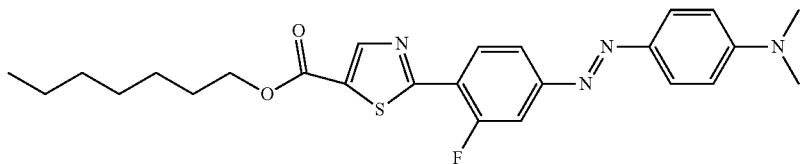

2-99

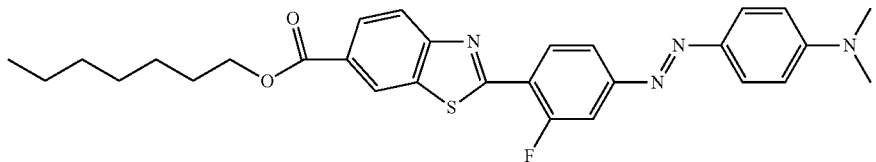

2-100

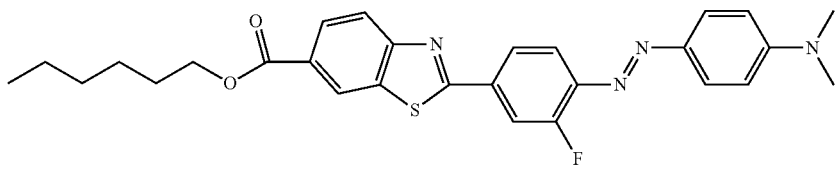

2-101

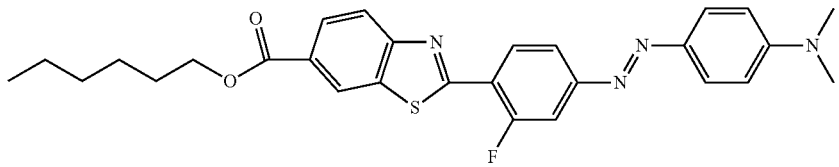

2-102

The compound represented by formula (1) is preferably at least one selected from the group consisting of compounds represented by any of formulae (2-2) to (2-7), (2-9) to (2-30), (2-34) to (2-42), and (2-47) to (2-102) among formulae (2-2) to (2-102), more preferably at least one selected from the group consisting of compounds represented by any of formulae (2-3) to (2-7), (2-9) to (2-30), (2-34) to (2-42), and (2-47) to (2-102), particularly preferably at least one selected from the group consisting of compounds represented by any of formulae (2-4) to (2-7), (2-9) to (2-30), (2-37) to (2-41), and (2-47) to (2-102), still more preferably at least one selected from the group consisting of compounds represented by any of (2-4) to (2-7), (2-9) to (2-30), (2-37) to (2-41), (2-47) to (2-65), and (2-75) to (2-102), and more particularly preferably at least one selected from the group consisting of compounds represented by any of formulae (2-4) to (2-7), (2-9) to (2-30), (2-47) to (2-65), and (2-75) to (2-102).

(Production Method)

A method for producing the compound represented by formula (1) (hereinafter, also referred to as compound (1)) will be described. Compound (1) can be produced, for example, from a compound represented by formula (1X) [hereinafter, also referred to as compound (1X)] and a compound represented by formula (1Y) [hereinafter, also referred to as compound (1Y)] by a process represented by the following reaction formula.

[Chemical formula 18]

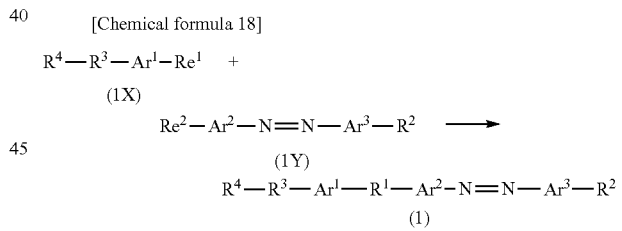

In the reaction formula, $Ar^1$, $Ar^2$, $Ar^3$, $R^1$, $R^2$, $R^3$, and $R^4$ have the same meanings as those in formula (1). $Re^1$ and $Re^2$ are a combination of groups that can react with each other to form a linking group or a single bond represented by $R^1$. Examples of the combination of $Re^1$ and $Re^2$ include the following. When $R^1$ is a single bond, examples of the combination of $Re^1$ and $Re^2$ include a combination of a dihydroxyboryl group or a dialkoxyboryl group and a halogen atom. When $R^1$ is —C(=O)O— or —OC(=O)—, examples of the combination of $Re^1$ and $Re^2$ include a combination of a carboxy group and a hydroxy group, a combination of a carbonyl halide group and a hydroxy group, and a combination of a carbonyloxyalkyl group and a hydroxy group. When $R^1$ is —C≡C—, examples of the combination of $Re^1$ and $Re^2$ include a combination of a halogen atom and an ethynyl group (—C≡CH). When $R^1$ is —CH=CH—, examples of the combination of $Re^1$ and $Re^2$ include a combination of a halogen atom and an ethenyl group (—CH=CH$_2$). When R$^1$ is —CH=N— or —N=CH—, examples of the combination of Re$^1$ and Re$^2$ include a combination of a formyl group and an amino group.

In the above reaction formula, the production method using compound (1X) having R$^4$—R$^3$— and compound (1Y) having R$^2$— has been described. However, compound (1) can also be produced by causing a compound obtained by protecting R$^4$—R$^3$— with an appropriate protecting group and a compound obtained by protecting R$^2$— with an appropriate protecting group to react with each other, and then performing an appropriate deprotection reaction.

As reaction conditions for causing compound (1X) and compound (1Y) to react with each other, optimum known conditions can be appropriately selected depending on the kinds of compound (1X) and compound (1Y) to be used.

For example, when R$^1$ is a single bond, Re$^1$ is a dihydroxyboryl group or a dialkoxyboryl group, and Re$^2$ is a halogen group, for example, the reaction conditions of Suzuki coupling can be used with reference to Netherton, M. R.; Fu, G. C. Org. Lett. 2001, 3 (26), 4295-4298 and the like. As a solvent, a mixed solvent of diethylene glycol dimethyl ether and water is used, and a Pd catalyst such as PdCl$_2$dppf is added in the presence of potassium acetate, followed by heating, whereby compound (1) can be obtained. A reaction temperature is selected depending on the kinds of compound (1X) and compound (1Y), and is, for example, in a range of room temperature to 160° C., and preferably in a range of 60° C. to 150° C. Reaction time is, for example, in a range of 15 minutes to 48 hours. Note that the same applies to a case where Re$^1$ is a halogen atom and Re$^2$ is a dihydroxyboryl group or a dialkoxyboryl group.

Note that compound (1X) in which Re$^1$ is a dihydroxyboryl group or a dialkoxyboryl group can be obtained, for example, by lithiating a bromo group in Ar$^1$ with n-butyllithium or the like and then causing trialkoxyborane to react with the lithiated product to introduce a dihydroxyboryl group or a dialkoxyboryl group. In addition, compound (1Y) in which Re$^2$ is a dihydroxyboryl group or a dialkoxyboryl group can be obtained, for example, by lithiating a bromo group in Ar$^2$ with n-butyllithium or the like and then causing a trialkoxyborane compound to react with the lithiated product to introduce a dihydroxyboryl group or a dialkoxyboryl group.

An azo structure in compound (1Y) can be constructed, for example, by converting an aromatic amine compound having a primary amino group into a diazonium salt with sodium nitrite or the like and diazo-coupling the diazonium salt with an aromatic compound with reference to description of production examples in paragraphs [0220] to [0268] of WO-A-2016/136561.

For example, as reaction conditions when R$^1$ is —C(=O)O—, Re$^1$ is a carboxy group, and Re$^2$ is a hydroxy group, a dehydration condensation reaction can be used with reference to Jiang, L.; Lu, X.; Zhang, H.; Jiang, Y.; Ma, D. J. Org. Chem. 2009, 74 (3), 4542-4546 and the like. Examples of the reaction conditions include conditions for condensation in a solvent in the presence of an esterification condensing agent. Examples of the solvent include a solvent in which both compound (1X) and compound (1Y) are soluble, such as chloroform. Examples of the esterification condensing agent include 1-ethyl-3-(3-dimethylaminopropyl) carbodiimide hydrochloride (EDC·HCl) and diisopropylcarbodiimide (IPC). Here, it is preferable to further use a base such as N,N-dimethylaminopyridine (DMAP) in combination. A reaction temperature is selected depending on the kinds of compound (1X) and compound (1Y), and is, for example, in a range of −15° C. to 70° C., and preferably in a range of 0° C. to 40° C. Reaction time is, for example, in a range of 15 minutes to 48 hours. Note that the same applies to a case where R$^1$ is —OC(=O)—, Re$^1$ is a hydroxy group, and Re$^2$ is a carboxy group.

For example, when R$^1$ is —C≡C—, Re$^1$ is an ethynyl group (—C≡CH), and Re$^2$ is a halogen atom, compound (1) can be synthesized by applying Sonogashira coupling using a Pd catalyst and a Cu catalyst. Note that the same applies to a case where Re$^1$ is a halogen atom and Re$^2$ is an ethynyl group (—C≡CH).

For example, when R$^1$ is —C=C—, Re$^1$ is an ethenyl group (—CH=CH$_2$), and Re$^2$ is a halogen group, compound (1) can be synthesized by applying a Heck reaction using a Pd catalyst and a phosphorus ligand. Note that the same applies to a case where Re$^1$ is a halogen atom and Re$^2$ is an ethenyl group (—CH=CH$_2$).

For example, when R$^1$ is —CH=N—, Re$^1$ is a formyl group, and Re$^2$ is an amino group, compound (1) can be synthesized by applying a general dehydration condensation reaction. Note that the same applies to a case where R$^1$ is —N=CH—, Re$^1$ is an amino group, and Re$^2$ is a formyl group.

When R$^3$ in the obtained compound (1) is an alkanediyloxycarbonyl group having 2 to 20 carbon atoms, R$^3$ can be changed to another alkanediyloxycarbonyl group having 2 to 20 carbon atoms by a general transesterification reaction. To the transesterification reaction, for example, with reference to Chen, C.-T.; Kuo, J.-H.; Ku, C.-H.; Weng, S.-S.; Liu, C.-Y. J. Org. Chem. 2005, 70 (4), 1328-1339 and the like, a method for heating compound (1) with an alcohol compound in a solvent using TiO(acac)$_2$ (name: bis(2,4-pentanedionato) titanium (IV) oxide) as a Lewis acid catalyst can be applied. As the solvent, a hydrocarbon-based aromatic compound such as xylene or toluene can be used. Note that the other alkanediyloxycarbonyl group having 2 to 20 carbon atoms includes a group having a different alkanediyl group moiety, and may have a different carbon number or different substituents.

The reaction time in the method for producing compound (1) can also be determined by appropriately sampling a reaction mixture in the middle of the reaction and confirming the degree of disappearance of compound (1X) and compound (1Y), the degree of generation of compound (1), and the like by a known analysis means such as liquid chromatography or gas chromatography.

From the reaction mixture after the reaction, compound (1) can be extracted by a known method such as recrystallization, reprecipitation, extraction, or various kinds of chromatography, or by appropriately combining these operations.

<Composition>

A composition containing the compound represented by formula (1) will be described. The composition according to the present embodiment contains the compound represented by formula (1) as, for example, a dye compound, and contains another component such as a liquid medium as necessary. The content of the compound represented by formula (1) in the composition is preferably 50 parts by mass or less, more preferably 0.1 parts by mass or more and 10 parts by mass or less, and still more preferably 0.1 parts by mass or more and 5 parts by mass or less based on 100 parts by mass of the solid matter of the composition. Within the above range, the compound represented by formula (1) can be sufficiently dispersed. As a result, it is possible to efficiently obtain a film containing the compound represented by formula (1) as a forming material and sufficiently suppressing generation of defects. Note that in the present specification, the solid matter refers to the total amount of components excluding a volatile component such as a solvent from the composition.

[Other Component]

(Other Dye Compound)

The composition may further contain another dye compound other than the compound represented by formula (1), for example, at least one dichroic dye. Examples of the other dye compound include an azo dye such as a monoazo dye, a bisazo dye, a trisazo dye, a tetrakis azo dye, or a stilbene azo dye, and at least one selected from the group consisting of these dyes is preferable. The composition may contain the other dye compound singly or in combination of two or more kinds thereof. For example, when the composition is used as an application type polarizing plate material, the other dye compound contained in the composition preferably has a maximum absorption wavelength in a wavelength range different from that of the compound represented by formula (1). When the composition is used as an application type polarizing plate material, the composition preferably contains three or more kinds of dichroic dyes in combination, including the compound represented by formula (1), and more preferably contains three or more kinds of azo dyes in combination. When the composition contains three or more kinds of dye compounds having different maximum absorption wavelengths in combination, for example, absorption can be obtained in the entire visible light region by a film formed from the composition.

When the composition contains the other dye compound, the content of the other dye compound is preferably 50 parts by mass or less, more preferably 0.1 parts by mass or more and 10 parts by mass or less, and still more preferably 0.1 parts by mass or more and 5 parts by mass or less based on 100 parts by mass of the solid matter of the composition. Within the above range, the other dye compound can be dispersed sufficiently.

(Polymerizable Liquid Crystal Compound)

The composition may contain at least one polymerizable liquid crystal compound in addition to the compound represented by formula (1). The polymerizable liquid crystal compound is a compound having a polymerizable group in a molecule thereof and capable of exhibiting a liquid crystal phase by being orientated. The polymerizable liquid crystal compound is preferably a compound capable of exhibiting a liquid crystal phase by being orientated alone. The composition may contain only one kind of polymerizable liquid crystal compound, or may contain two or more kinds of polymerizable liquid crystal compounds.

The polymerizable group means a group involved in a polymerization reaction, and is preferably a photopolymerizable group. Here, the polymerizable group refers to a group that can be involved in a polymerization reaction by an active radical, an acid, or the like generated from a polymerization initiator described later. Examples of the polymerizable group include a vinyl group, a vinyloxy group, a 1-chlorovinyl group, an isopropenyl group, a 4-vinylphenyl group, an acryloyloxy group, a methacryloyloxy group, an oxiranyl group, and an oxetanyl group. Among these groups, the polymerizable group is preferably at least one selected from the group consisting of an acryloyloxy group, a methacryloyloxy group, a vinyloxy group, an oxiranyl group, and an oxetanyl group, and more preferably an acryloyloxy group.

The polymerizable liquid crystal compound may be a compound that can constitute a thermotropic liquid crystal type polymer, or may be a compound that can constitute a lyotropic liquid crystal type polymer.

The polymerizable liquid crystal compound may be a compound exhibiting a nematic liquid crystal phase, a compound exhibiting a smectic liquid crystal phase, or a compound exhibiting both a nematic liquid crystal phase and a smectic liquid crystal phase. The polymerizable liquid crystal compound is preferably a compound exhibiting a smectic liquid crystal phase, and more preferably a compound exhibiting a high-order smectic liquid crystal phase. The composition containing a polymerizable liquid crystal compound exhibiting a smectic liquid crystal phase can provide a polarizing film having better polarizing performance.

The compound represented by formula (1) can exhibit high dichroism even in a state of being dispersed between dense molecular chains formed from a polymerizable liquid crystal compound exhibiting a smectic liquid crystal phase. Therefore, a composition containing the compound represented by formula (1) and a polymerizable liquid crystal compound, particularly a polymerizable liquid crystal compound exhibiting a smectic liquid crystal phase can provide a polarizing film having a high dichroic ratio.

Examples of the high-order smectic liquid crystal phase include a smectic B phase, a smectic D phase, a smectic E phase, a smectic F phase, a smectic G phase, a smectic H phase, a smectic I phase, a smectic J phase, a smectic K phase, and a smectic L phase. Among these phases, a smectic B phase, a smectic F phase, and a smectic I phase are preferable, and a smectic B phase is more preferable. When the smectic liquid crystal phase exhibited by a polymerizable liquid crystal compound is any one of these high-order smectic phases, a polarizing film having a higher degree of orientation order can be obtained. A polarizing film obtained from a composition containing a polymerizable liquid crystal compound exhibiting a high-order smectic liquid crystal phase having a high degree of orientation order exhibits a Bragg peak derived from a high-order structure such as a hexatic phase or a crystal phase in X-ray diffraction measurement. The Bragg peak is a peak derived from a plane periodic structure of molecular orientation. A periodic interval (order period) of a polarizing film obtained from the composition is preferably 0.30 nm or more and 0.60 nm or less.

The kind of liquid crystal phase exhibited by a polymerizable liquid crystal compound can be confirmed, for example, by the following method. That is, an appropriate substrate is prepared, a solution containing a polymerizable liquid crystal compound and a solvent is applied to the substrate to form a coating film, and then the coating film is subjected to heat treatment or pressure reducing treatment to remove the solvent contained in the coating film. Subsequently, the coating film formed on the substrate is heated to an isotropic phase temperature, and then gradually cooled to develop a liquid crystal phase. The liquid crystal phase is tested by texture observation with a polarizing microscope, X-ray diffraction measurement, or differential scanning calorimetry. In this test, for example, it can be confirmed that the coating film exhibits a nematic liquid crystal phase by being cooled to a first temperature, and that the coating film exhibits a smectic liquid crystal phase by being further gradually cooled to a second temperature.

The polymerizable liquid crystal compound is preferably a compound represented by formula (4) (hereinafter, also referred to as "compound (4)"):

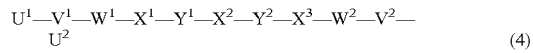

wherein $X^1$, $X^2$, and $X^3$ each independently represent a 1,4-phenylene group optionally having a substituent or a cyclohexane-1,4-diyl group optionally having a substituent, provided that at least one of $X^1$, $X^2$, and $X^3$ is a 1,4-phenylene group optionally having a substituent; at least one of —$CH_2$-s constituting the cyclohexane-1,4-diyl group may be substituted with —O—, —S—, or —NR—; Here, R represents an alkyl group having 1 to 6 carbon atoms or a phenyl group.

$Y^1$ and $Y^2$ each independently represent a single bond, —$CH_2CH_2$—, —$CH_2O$—, —(C=O)O—, —O(C=O)O—, —N=N—, —$CR^a$=$CR^b$, —C≡C—, or —$CR^a$=N—; $R^a$ and $R^b$ each independently represent a hydrogen atom or an alkyl group having 1 to 4 carbon atoms;

$U^1$ represents a hydrogen atom or a polymerizable group;

$U^2$ represents a polymerizable group;

$W^1$ and $W^2$ each independently represent a single bond, —O—, —S—, —(C=O)O—, or —O(C=O)O—; and $V^1$ and $V^2$ each independently represent an alkanediyl group having 1 to 20 carbon atoms and optionally having a substituent, and —$CH_2$— constituting the alkanediyl group may be substituted with —O—, —S—, or —NH—.)

The 1,4-phenylene group optionally having a substituent is preferably a 1,4-phenylene group having no substituent. The cyclohexane-1,4-diyl group optionally having a substituent is preferably a trans-cyclohexane-1,4-diyl group optionally having a substituent. The trans-cyclohexane-1,4-diyl group optionally having a substituent is preferably a trans-cyclohexane-1,4-diyl group having no substituent.

Examples of the substituent optionally included in the 1,4-phenylene group optionally having a substituent or the cyclohexane-1,4-diyl group optionally having a substituent include an alkyl group having 1 to 4 carbon atoms, such as a methyl group, an ethyl group, or a n-butyl group, a cyano group, and a halogen atom.

$Y^1$ is preferably a single bond, —$CH_2CH_2$—, or —(C=O)O—, and $Y^2$ is preferably —$CH_2H_2$— or —$CH_2O$—.

$U^1$ is a hydrogen atom or a polymerizable group, and preferably a polymerizable group. $U^2$ is a polymerizable group. $U^1$ and $U^2$ are preferably both polymerizable groups, and more preferably both photopolymerizable groups. A polymerizable liquid crystal compound having a photopolymerizable group is advantageous in that the polymerizable liquid crystal compound having a photopolymerizable group can be polymerized under lower temperature conditions.

The polymerizable groups represented by $U^1$ and $U^2$ may be different from each other, but are preferably the same as each other. Examples of the polymerizable group include a vinyl group, a vinyloxy group, a 1-chlorovinyl group, an isopropenyl group, a 4-vinylphenyl group, an acryloyloxy group, a methacryloyloxy group, an oxiranyl group, and an oxetanyl group. Among these groups, each of the polymerizable groups represented by $U^1$ and $U^2$ is preferably at least one selected from the group consisting of a vinyloxy group, an acryloyloxy group, a methacryloyloxy group, an oxiranyl group, and an oxetanyl group, and more preferably an acryloyloxy group.

Examples of the alkanediyl group represented by $V^1$ and $V^2$ include a methylene group, an ethylene group, a propane-1,3-diyl group, a butane-1,3-diyl group, a butane-1,4-diyl group, a pentane-1,5-diyl group, a hexane-1,6-diyl group, a heptane-1,7-diyl group, an octane-1,8-diyl group, a decane-1,10-diyl group, a tetradecane-1,1-diyl group, and an icosane-1,20-diyl group. $V^1$ and $V^2$ are each preferably an alkanediyl group having 2 to 12 carbon atoms, and more preferably an alkanediyl group having 6 to 12 carbon atoms.

Examples of the substituent optionally included in the alkanediyl group having 1 to 20 carbon atoms and optionally having a substituent include a cyano group and a halogen atom. The alkanediyl group is preferably an alkanediyl group having no substituent, and more preferably a linear alkanediyl group having no substituent.

$W^1$ and $W^2$ are each independently preferably a single bond or —O—.

Specific examples of compound (4) include compounds represented by the following formulae (4-1) to (4-43). When compound (4) has a cyclohexane-1,4-diyl group, the cyclohexane-1,4-diyl group is preferably a trans type.

[Chemical formula 19]

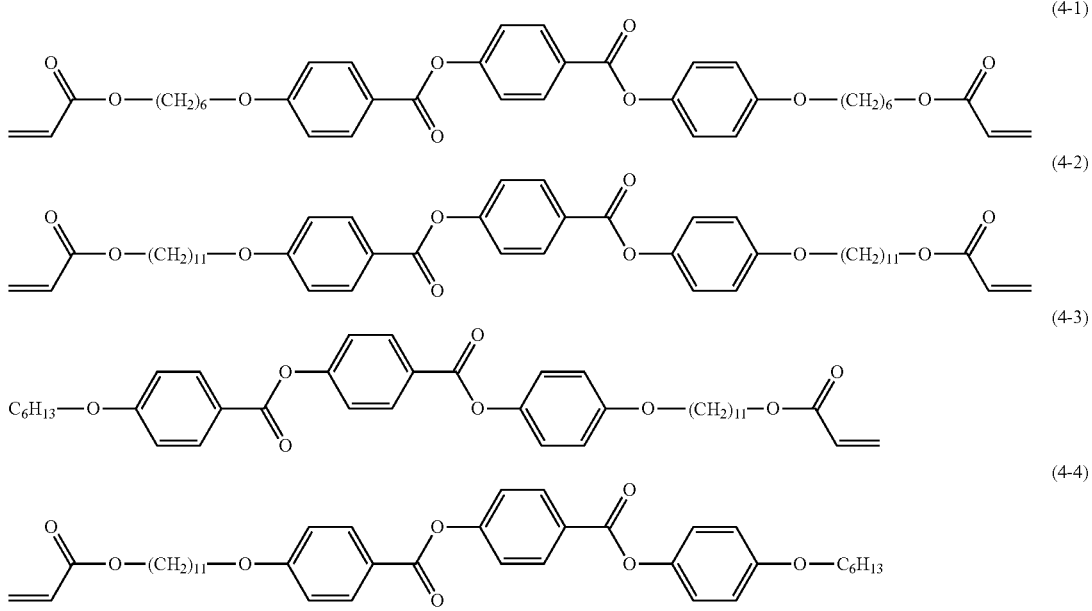

[Chemical formula 20]
(4-5)
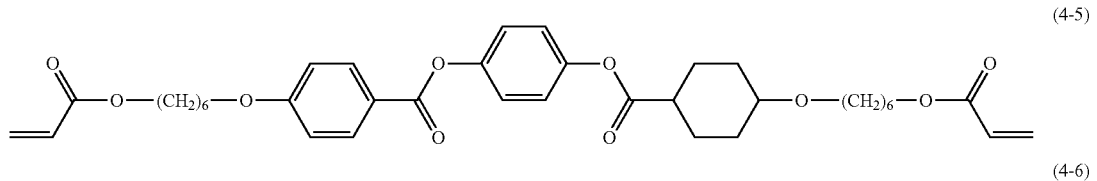
(4-6)
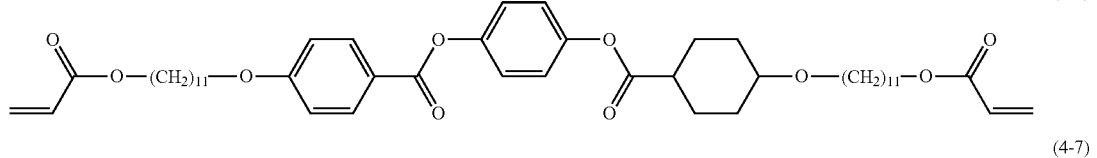
(4-7)
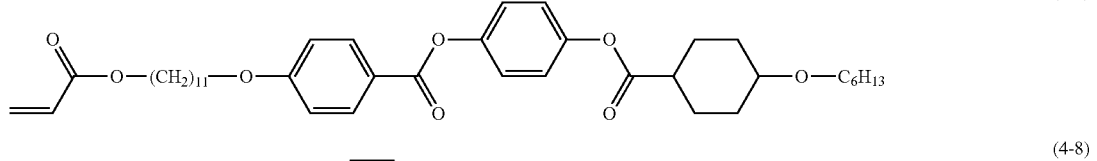
(4-8)
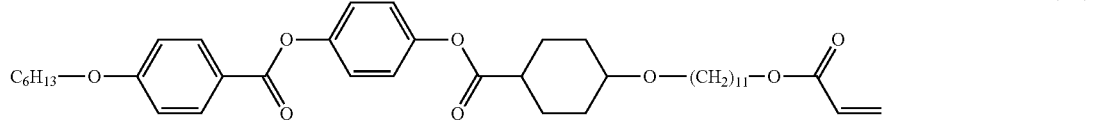
[Chemical formula 21]
(4-9)
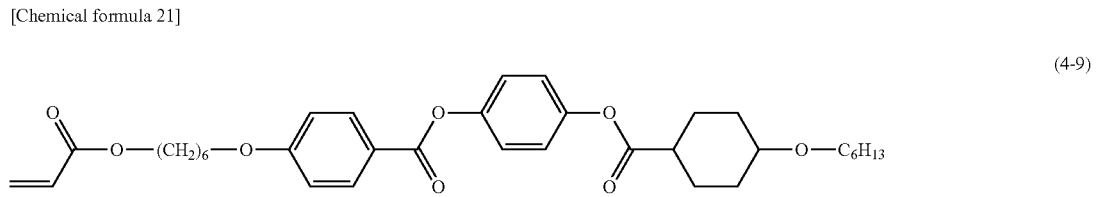
(4-10)
(4-11)
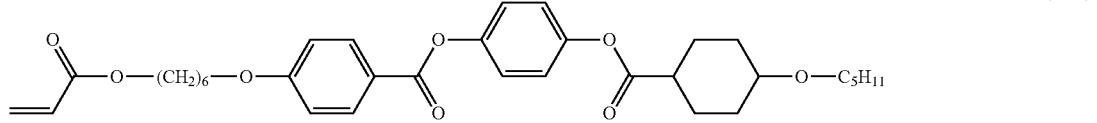
[Chemical formula 22]
(4-12)
(4-13)
(4-14)
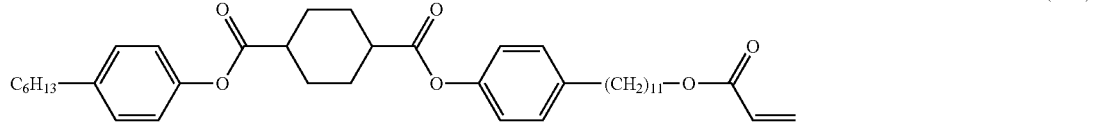

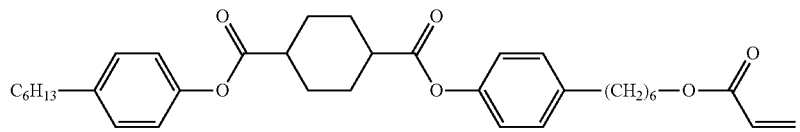
(4-15)
[Chemical formula 23]
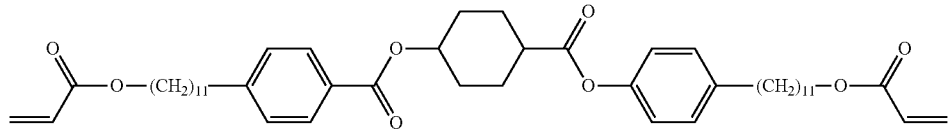
(4-16)
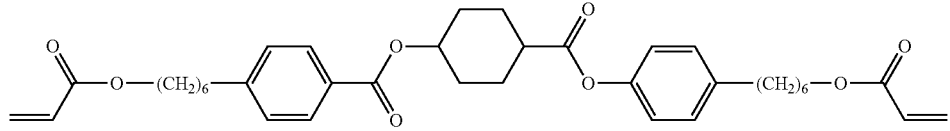
(4-17)
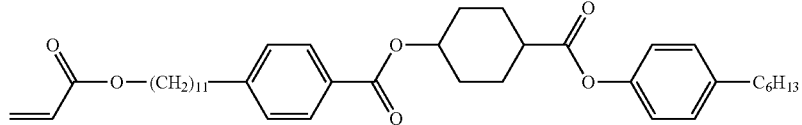
(4-18)
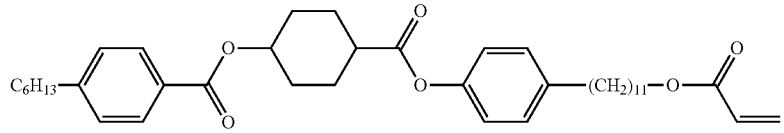
(4-19)
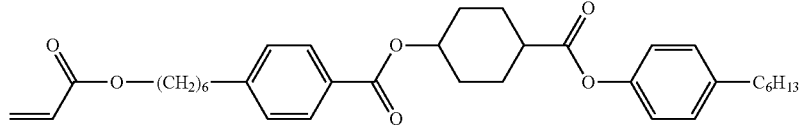
(4-20)
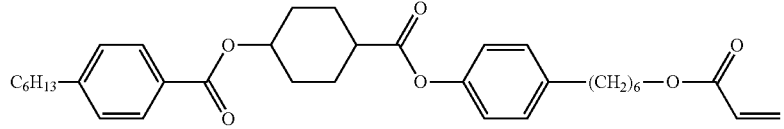
(4-21)
[Chemical formula 24]
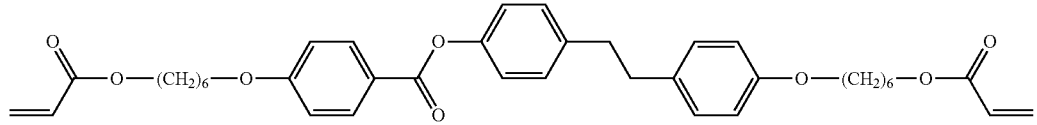
(4-22)
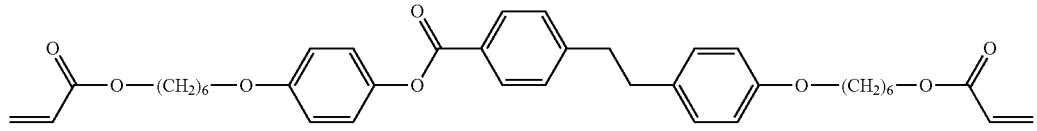
(4-23)
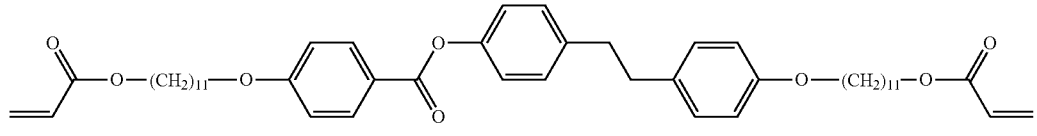
(4-24)

(4-25)
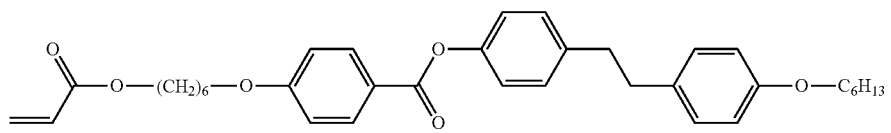
(4-26)
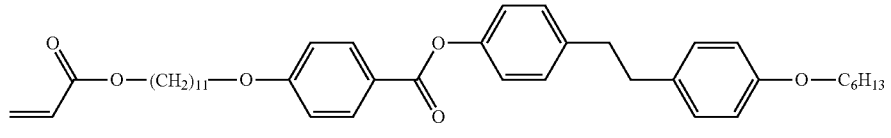
[Chemical formula 25]
(4-27)
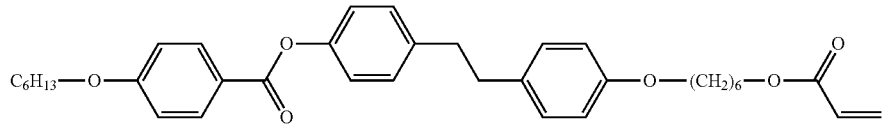
(4-28)
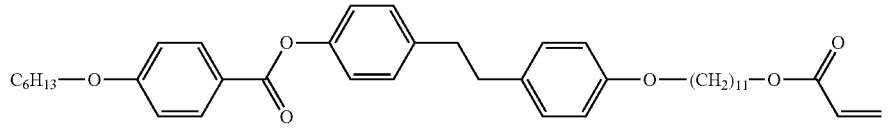
(4-29)
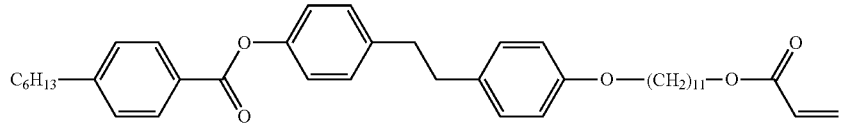
(4-30)
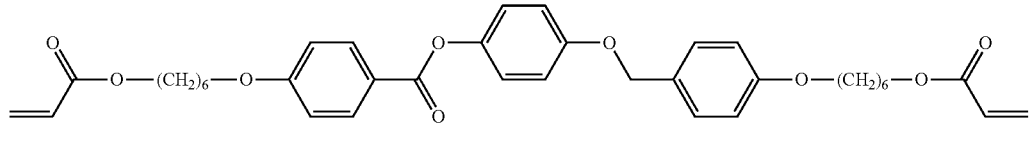
(4-31)
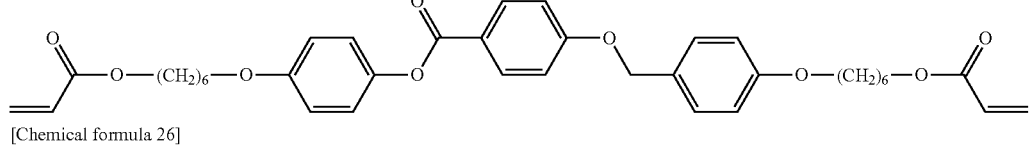
[Chemical formula 26]
(4-32)
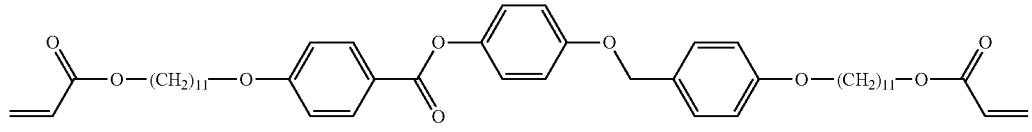
(4-33)
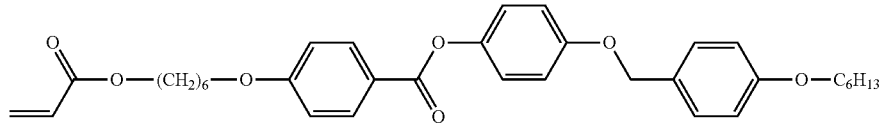
(4-34)
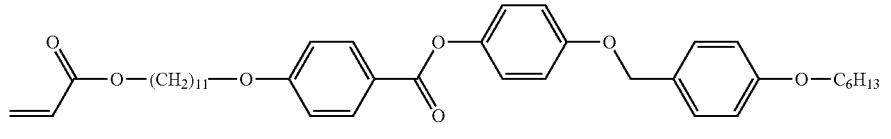
(4-35)
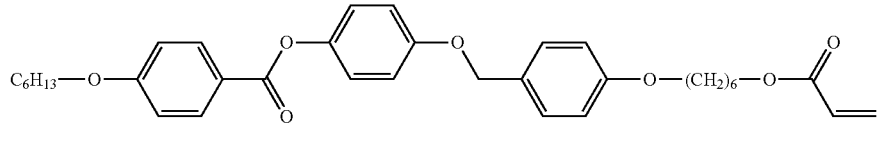

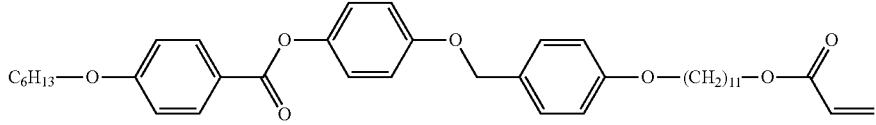
(4-36)

[Chemical formula 27]

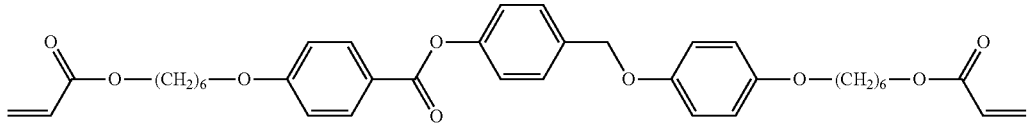
(4-37)

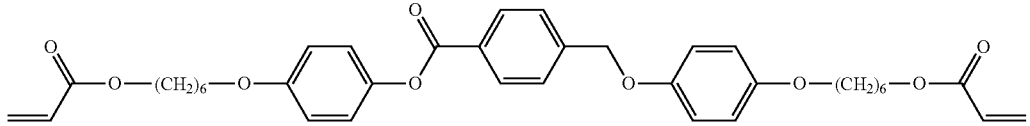
(4-38)

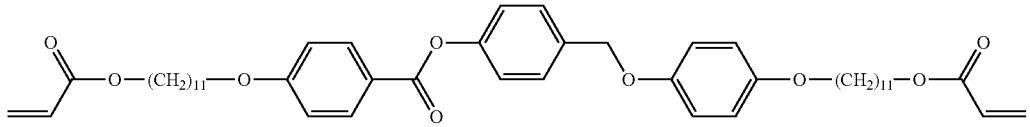
(4-39)

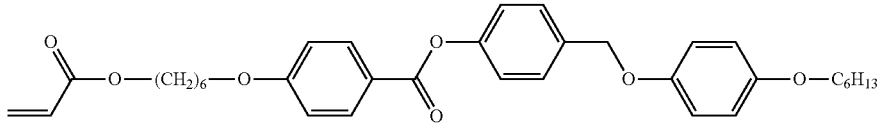
(4-40)

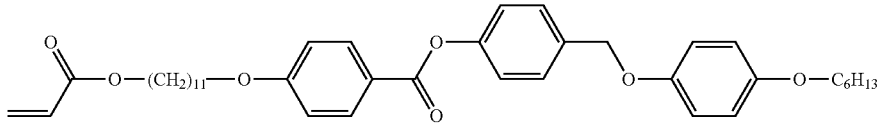
(4-41)

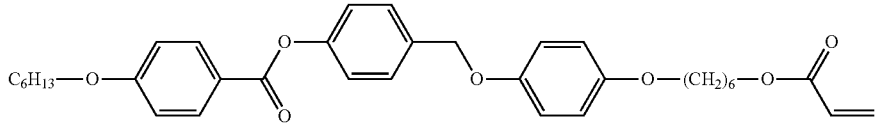
(4-42)

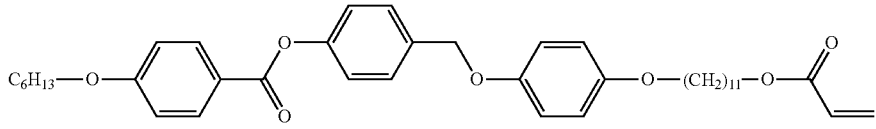
(4-43)

Among these compounds, compound (4) is preferably a compound represented by at least one selected from the group consisting of compounds represented by any of formulae (4-5), (4-6), (4-7), (4-8), (4-9), (4-10), (4-11), (4-12), (4-13), (4-14), (4-15), (4-22), (4-24), (4-25), (4-26), (4-27), (4-28), and (4-29).

Compound (4) can be produced, for example, by a method described in a known document such as Lub et al. Recl. Trav. Chim. Pays-Bas, 115, 321-328(1996) or JP-B2-4719156.

The composition may contain two or more kinds of polymerizable liquid crystal compounds. When two or more kinds of polymerizable liquid crystal compounds are used in combination, at least one of the polymerizable liquid crystal compounds is preferably compound (4), and two or more kinds of the polymerizable liquid crystal compounds are each more preferably compound (4). By using two or more kinds of polymerizable liquid crystal compounds in combination, the liquid crystal phase may be temporarily retained even at a temperature equal to or lower than a liquid crystal-crystal phase transition temperature. The total content of compound (4) contained in the composition is preferably 40% by mass or more, and more preferably 60% by mass or more based on the total mass of all the polymerizable liquid crystal compounds in the composition, and all the polymerizable liquid crystal compounds may be each compound (4). When the content of compound (4) is within the above range, the polymerizable liquid crystal compounds are likely to be aligned with a high degree of orientation order, and the compound represented by formula (1) is orientated along the polymerizable liquid crystal compounds, whereby a polarizing film having excellent polarizing performance can be obtained.

The content ratio of a polymerizable liquid crystal compound in the composition is preferably 70 parts by mass or more and 99.5 parts by mass or less, more preferably 80 parts by mass or more and 99 parts by mass or less, and still more preferably 80 parts by mass or more and 94 parts by mass or less based on 100 parts by mass of the solid matter of the composition from a viewpoint of enhancing orientation of the polymerizable liquid crystal compound.

(Polymer Compound)

The composition may further contain a polymer compound in addition to the compound represented by formula (1). When the composition contains a polymer compound, it is possible to constitute a composition in which the compound represented by the formula (1) is dispersed in the polymer compound.

The polymer compound that can be contained in the composition is not particularly limited as long as the polymer compound can disperse the compound represented by formula (1), and examples of the polymer compound include: a polyolefin such as polyethylene or polypropylene; a cyclic olefin resin such as a norbornene polymer; polyalkylene ether and polyvinyl alcohol; polymethacrylate; and polyacrylate. These polymer compounds each have a liquid crystalline organic group. Among these polymer compounds, polymethacrylate and polyacrylate are preferable from a viewpoint of easily dispersing the compound represented by formula (1) uniformly. One kind or two or more kinds of polymer compounds may be contained in the composition.

The polymer compound that can be contained in the composition may be a liquid crystalline polymer compound, and examples of the liquid crystalline polymer compound include a polymer of the polymerizable liquid crystal compound. One kind or two or more kinds of the polymerizable liquid crystal compounds as a constituent monomer of the polymer of the polymerizable liquid crystal compound may be used. The composition may contain the polymerizable liquid crystal compound and a polymer thereof.

The polymer compound has a weight average molecular weight of, for example, 10,000 or more and 200,000 or less, preferably 20,000 or more and 150,000 or less in terms of polystyrene.

When the composition contains a polymer compound, the content of the polymer compound can be appropriately selected depending on a purpose and the like. The content of the polymer compound is preferably 70 parts by mass or more and 99.5 parts by mass or less, more preferably 80 parts by mass or more and 99 parts by mass or less, and still more preferably 80 parts by mass or more and 94 parts by mass or less based on 100 parts by mass of the solid matter of the composition.

When the composition contains compound (1) and a polymerizable liquid crystal compound, the content of compound (1) in the composition is usually 0.1 parts by mass or more and 50 parts by mass or less, preferably 0.1 parts by mass or more and 20 parts by mass or less, more preferably 0.1 parts by mass or more and 10 parts by mass or less, and still more preferably 0.1 parts by mass or more and 5 parts by mass or less based on 100 parts by mass of the polymerizable liquid crystal compound. When the content of compound (1) is 50 parts by mass or less based on 100 parts by mass of the polymerizable liquid crystal compound, there is a tendency that it is possible to obtain a film having a small orientation disorder of the polymerizable liquid crystal compound and compound (1) and having a high degree of orientation order.

When the composition contains compound (1) and a polymer compound, the content of compound (1) in the composition is usually 0.1 parts by mass or more and 50 parts by mass or less, preferably 0.1 parts by mass or more and 20 parts by mass or less, more preferably 0.1 parts by mass or more and 10 parts by mass or less, and still more preferably 0.1 parts by mass or more and 5 parts by mass or less based on 100 parts by mass of the polymer compound.

In a case where the polymer compound is a liquid crystalline polymer compound, when the content of compound (1) is 50 parts by mass or less based on 100 parts by mass of the liquid crystalline polymer compound, there is a tendency that it is possible to obtain a film having a small orientation disorder of the liquid crystalline polymer compound and compound (1) and having a high degree of orientation order.

The composition preferably further contains a liquid medium such as a solvent and a polymerization initiator, and may further contain a photosensitizer, a polymerization inhibitor, a leveling agent, and the like as necessary.

(Solvent)

The solvent is preferably a solvent capable of completely dissolving compound (1), a polymerizable liquid crystal compound, and a polymer compound. In addition, the solvent is preferably inert to a polymerization reaction of the polymerizable liquid crystal compound.

Examples of the solvent include: an alcohol solvent such as methanol, ethanol, ethylene glycol, isopropyl alcohol, propylene glycol, ethylene glycol methyl ether, ethylene glycol butyl ether, or propylene glycol monomethyl ether; an ester solvent such as ethyl acetate, butyl acetate, ethylene glycol methyl ether acetate, γ-butyrolactone, propylene glycol methyl ether acetate, or ethyl lactate; a ketone solvent such as acetone, methyl ethyl ketone, cyclopentanone, cyclohexanone, 2-heptanone, or methyl isobutyl ketone; an aliphatic hydrocarbon solvent such as pentane, hexane, or heptane; an aromatic hydrocarbon solvent such as toluene or xylene; a nitrile solvent such as acetonitrile; an ether solvent such as tetrahydrofuran or dimethoxyethane; and a chlorine-containing solvent such as chloroform or chlorobenzene. These solvents may be used singly or in combination of two or more kinds thereof.

When the composition contains the solvent, the content ratio of the solvent is preferably 50% by mass or more and 98% by mass or less based on the total amount of the composition. In other words, the content ratio of the solid matter in the composition is preferably 2% by mass or more and 50% by mass or less. When the solid matter is 50% by mass or less, the viscosity of the composition decreases, the thickness of a film obtained from the composition is substantially uniform, and unevenness tends to be hardly generated in the film. The content ratio of the solid matter can be determined in consideration of the thickness of a film to be produced.

(Polymerization Initiator)

The polymerization initiator is a compound capable of initiating a polymerization reaction of a polymerizable liquid crystal compound. The polymerization initiator is preferably a photopolymerization initiator in that the photopolymerization initiator can initiate a polymerization reaction under lower temperature conditions. Specific examples of the photopolymerization initiator include a photopolymerization initiator capable of generating an active radical or an acid by action of light. Among these photopolymerization initiators, a photopolymerization initiator that generates a radical by action of light is preferable.

Examples of the polymerization initiator include a benzoin compound, a benzophenone compound, an alkylphenone compound, an acylphosphine oxide compound, a triazine compound, an iodonium salt, and a sulfonium salt. The polymerization initiator can be appropriately selected from known polymerization initiators depending on a purpose and the like. In addition, the polymerization initiator may be used singly or in combination of two or more kinds thereof.

Examples of the benzoin compound include benzoin, benzoin methyl ether, benzoin ethyl ether, benzoin isopropyl ether, and benzoin isobutyl ether.

Examples of the benzophenone compound include benzophenone, methyl o-benzoylbenzoate, 4-phenylbenzophenone, 4-benzoyl-4'-methyldiphenylsulfide, 3,3,4,4-tetra(tert-butylperoxycarbonyl) benzophenone, and 2,4,6-trimethylbenzophenone.

Examples of the alkylphenone compound include oligomers of diethoxyacetophenone, 2-methyl-2-morpholino-1-(4-methylthiophenyl) propan-1-one, 2-benzyl-2-dimethylamino-1-(4-morpholinophenyl) butan-1-one, 2-hydroxy-2-methyl-1-phenylpropan-1-one, 1,2-diphenyl-2,2-dimethoxyethan-1-one, 2-hydroxy-2-methyl-1-[4-(2-hydroxyethoxy) phenyl] propan-1-one, 1-hydroxycyclohexylphenyl ketone, and 2-hydroxy-2 methyl-1-[4-(1-methylvinyl) phenyl] propan-1-one.

Examples of the acylphosphine oxide compound include 2,4,6-trimethylbenzoyldiphenylphosphine oxide and bis(2, 4,6-trimethylbenzoyl) phenylphosphine oxide.

Examples of the triazine compound include 2,4-bis (trichloromethyl)-6-(4-methoxyphenyl)-1,3,5-triazine, 2,4-bis(trichloromethyl)-6-(4-methoxynaphthyl)-1,3,5-triazine, 2,4-bis(trichloromethyl)-6-(4-methoxystyryl)-1,3,5-triazine, 2,4-bis(trichloromethyl)-6-[2-(5-methylfuran-2-yl) ethenyl]-1,3,5-triazine, 2,4-bis(trichloromethyl)-6-[2-(furan-2-yl) ethenyl]-1,3,5-triazine, 2,4-bis(trichloromethyl)-6-[2-(4-diethylamino-2-methylphenyl) ethenyl]-1,3,5-triazine, and 2,4-bis(trichloromethyl)-6-[2-(3,4-dimethoxyphenyl) ethenyl]-1,3,5-triazine.

Examples of the iodonium salt and the sulfonium salt include salts represented by the following formulae.

[Chemical formula 28]

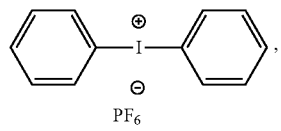

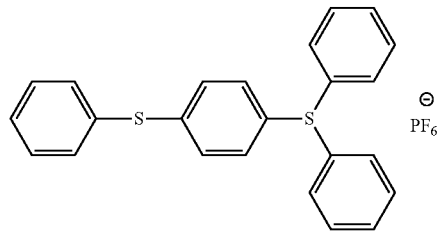

As the polymerization initiator, a commercially available product can also be used. Examples of the commercially available polymerization initiator include: Irgacures (registered trademark) 907, 184, 651, 819, 250, and 369 (manufactured by BASF Japan Ltd.); SEIKUOLs (registered trademark) BZ, Z, and BEE (manufactured by Seiko Chemical Co., Ltd.); Kayacures (registered trademark) BP100 and UVI-6992 (manufactured by The Dow Chemical Company); ADEKA OPTOMERs SP-152 and SP-170 (manufactured by ADEKA Corporation); TAZ-A and TAZ-PP (manufactured by Nihon SiberHegner K.K.); and TAZ-104 (manufactured by Sanwa Chemical Co., Ltd.).

When the composition contains a polymerization initiator, the content of the polymerization initiator only needs to be appropriately determined depending on the kind and amount of a polymerizable liquid crystal compound contained in the composition. The content of the polymerization initiator is, for example, 0.001 parts by mass or more, 0.01 parts by mass or more, or 0.1 parts by mass or more, and is, for example, 30% by mass or less, 10% by mass or less, or 8% by mass or less based on 100 parts by mass of the polymerizable liquid crystal compound. In addition, the content of the polymerization initiator is preferably 0.001 parts by mass or more and 30 parts by mass or less, more preferably 0.01 parts by mass or more and 10 parts by mass or less, and still more preferably 0.1 parts by mass or more and 8 parts by mass or less based on 100 parts by mass of the polymerizable liquid crystal compound. When the content of the polymerizable initiator is within the above range, the polymerizable liquid crystal compound can be polymerized without causing orientation disorder for the polymerizable liquid crystal compound.

(Photosensitizer)

When the composition contains a photopolymerization initiator, the composition may preferably contain at least one photosensitizer. When the composition contains a photopolymerization initiator and a photosensitizer, a polymerization reaction of a polymerizable liquid crystal compound tends to be further promoted. Examples of the photosensitizer include a xanthone compound such as xanthone or thioxanthone (for example, 2,4-diethylthioxanthone or 2-isopropylthioxanthone); an anthracene compound such as anthracene or an alkoxy group-containing anthracene (for example, dibutoxyanthracene); and phenothiazine and rubrene. The photosensitizer can be used singly or in combination of two or more kinds thereof.

When the composition contains a photosensitizer, the content of the photosensitizer in the composition only needs to be appropriately determined depending on the kinds and amounts of a photopolymerization initiator and a polymerizable liquid crystal compound. The content of the photosensitizer in the composition is preferably 0.1 parts by mass or more and 30 parts by mass or less, more preferably 0.5 parts by mass or more and 10 parts by mass or less, and still more preferably 0.5 parts by mass or more and 8 parts by mass or less based on 100 parts by mass of the polymerizable liquid crystal compound.

(Polymerization Inhibitor)

The composition may contain at least one polymerization inhibitor. Examples of the polymerization inhibitor include a radical scavenger such as hydroquinone, an alkoxy group-containing hydroquinone, an alkoxy group-containing catechol (for example, butylcatechol), pyrogallol, or a 2,2,6,6-tetramethyl-1-piperidinyloxy radical; a thiophenol; and a R-Naphthylamine and a 0-naphthol.

When the composition contains a polymerization inhibitor, the degree of progress of a polymerization reaction of a polymerizable liquid crystal compound can be controlled.

When the composition contains a polymerization inhibitor, the content of the polymerization inhibitor in the composition is preferably 0.1 parts by mass or more and 30 parts by mass or less, more preferably 0.5 parts by mass or more and 10 parts by mass or less, and still more preferably 0.5 parts by mass or more and 8 parts by mass or less based on 100 parts by mass of the polymerizable liquid crystal compound.

(Leveling Agent)

The composition may contain at least one leveling agent. The leveling agent has a function of adjusting fluidity of the composition and making a coating film obtained by applying the composition flatter, and specific examples of the leveling agent include a surfactant. The leveling agent is preferably at least one selected from the group consisting of a leveling agent containing a polyacrylate compound as a main component and a leveling agent containing a fluorine atom-containing compound as a main component. The leveling agent can be used singly or in combination of two or more kinds thereof.

Examples of the leveling agent containing a polyacrylate compound as a main component include "BYK-350", "BYK-352", "BYK-353", "BYK-354", "BYK-355", "BYK-358N", "BYK-361N", "BYK-380", "BYK-381", and "BYK-392" (BYK Chemie).

Examples of the leveling agent containing a fluorine atom-containing compound as a main component include "Megafac (registered trademark) R-08", "Megafac R-30", "Megafac R-90", "Megafac F-410", "Megafac F-411", "Megafac F-443", "Megafac F-445", "Megafac F-470", "Megafac F-471", "Megafac F-477", "Megafac F-479", "Megafac F-482", and "Megafac F-483" (DIC Corporation); "SURFLON (registered trademark) S-381", "SURFLON S-382", "SURFLON S-383", "SURFLON S-393", "SURFLON SC-101", "SURFLON SC-105", "SURFLON KH-40", and "SURFLON SA-100" (AGC Seimi Chemical Co., Ltd.); "E1830" and "E5844" (DAIKIN FINE CHEMICAL LABORATORIES); and "F-top EF301", "F-top EF303", "F-top EF351", and "F-top EF352" (manufactured by Mitsubishi Materials Electronic Chemicals Co., Ltd.).

When the composition contains a leveling agent, the content of the leveling agent is preferably 0.05 parts by mass or more and 5 parts by mass or less, and more preferably 0.05 parts by mass or more and 3 parts by mass or less based on 100 parts by mass of the total amount of the polymerizable liquid crystal compound and the polymer compound. When the content of the leveling agent is within the above range, the polymerizable liquid crystal compound is easily horizontally orientated, unevenness tends to be hardly generated, and a smoother film, for example, a polarizing film tends to be obtained.

When the content of the leveling agent is within the above range, the polymerizable liquid crystal compound or the liquid crystalline polymer compound such as a polymer of the polymerizable liquid crystal compound is easily horizontally orientated, and an obtained film tends to be smoother. When the content of the leveling agent based on the polymerizable liquid crystal compound exceeds the above range, unevenness may be easily generated in an obtained film.

The composition may contain another additive other than those described above. Examples of the other additive include a release agent, a stabilizer, an antioxidant, a colorant such as a bluing agent, a flame retardant, and a lubricant. When the composition contains the other additive, the content of the other additive is preferably more than 0% and 20% by mass or less, and more preferably more than 0% and 10% by mass or less based on the solid matter of the composition.

<Film>

A film according to the present embodiment is obtained using a compound represented by formula (1) as a forming material, and may constitute, for example, a polarizing film. That is, the film may be a film formed of the compound represented by formula (1), a film formed of a composition containing the compound represented by formula (1), or a cured product of a composition containing the compound represented by formula (1). The film formed of the compound represented by formula (1) may be formed by applying the compound represented by formula (1) to a substrate to form a film. In addition, the film formed of the composition containing the compound represented by formula (1) may be formed by applying the composition to a substrate to form a film. In addition, when the composition containing the compound represented by formula (1) contains a polymerizable liquid crystal compound, a film containing a cured product obtained by polymerizing the polymerizable liquid crystal compound may be formed by applying the composition to a substrate, forming a film, and then polymerizing and curing the polymerizable liquid crystal compound.

<Laminate>

A laminate according to the present embodiment includes a film containing the compound represented by formula (1) as a forming material.

The laminate may include a substrate and a film which is disposed on the substrate and contains the compound represented by formula (1) as a forming material. The laminate can constitute, for example, a polarizing plate. The laminate can be produced by applying a composition containing the compound represented by formula (1) onto a substrate to form a film of the applied composition.

The laminate according to the present embodiment can be produced by a production method including the following steps A and B, and further including step C as necessary. When the composition contains a liquid crystalline polymer compound in addition to a compound represented by formula (1), the liquid crystalline polymer compound is preferably further orientated in step B. When the composition contains a polymerizable liquid crystal compound in addition to the compound represented by formula (1), the production method preferably includes steps A, B, and C.

The laminate is produced by a production method including:
  step A: a step of applying a composition containing at least compound (1) to a surface of a substrate to form a coating film;
  step B: a step of orientating at least one of a liquid crystalline polymer compound and a polymerizable liquid crystal compound, and compound (1) contained in the formed coating film while removing a solvent by heating; and
  step C: irradiating the orientated polymerizable liquid crystal compound with an active energy ray to polymerize the polymerizable liquid crystal compound.

(Step A)

The substrate may be any of a glass substrate, a resin substrate, and the like, and is preferably a resin substrate. By using a film substrate formed of a resin, a thin laminate can be obtained.

The resin substrate is preferably a transparent resin substrate. The transparent resin substrate means a substrate having translucency capable of transmitting light, particularly visible light, and the translucency refers to a characteristic that visibility correction transmittance for light in a wavelength range of 380 nm or more and 780 nm or less is 80% or more.

Examples of the resin constituting the substrate include: a polyolefin such as polyethylene, polypropylene, or a norbornene-based polymer; a cyclic olefin-based resin; polyvinyl alcohol; polyethylene terephthalate; polymethacrylate; polyacrylate; a cellulose ester such as triacetyl cellulose, diacetyl cellulose, or cellulose acetate propionate; polyethylene naphthalate; polycarbonate; polysulfone; polyethersulfone; polyether ketone; polyphenylene sulfide; and polyphenylene oxide. The resin constituting the substrate is preferably at least one selected from the group consisting of a cellulose ester, a cyclic olefin-based resin, polycarbonate, polyethersulfone, polyethylene terephthalate, and polymethacrylate.

The thickness of the substrate is preferably thin as long as the substrate can be practically handled. However, if the substrate is too thin, the strength thereof may be reduced and workability may be poor. The thickness of the substrate is usually 5 µm or more and 300 µm or less, and preferably 20 µm or more and 200 µm or less.

(Step B)

When the composition contains a solvent, the solvent is usually removed from a formed coating film. Examples of a method for removing the solvent include a natural drying method, a forced-air drying method, a heat drying method, and a reduced-pressure drying method.

When the formed coating film contains a liquid crystalline polymer compound and a polymerizable liquid crystal compound, the coating film is usually heated to a temperature equal to or higher than a temperature at which the polymerizable liquid crystal compound and the liquid crystalline polymer compound transition to a solution state, and subsequently cooled to a temperature at which the polymerizable liquid crystal compound and the liquid crystalline polymer compound are liquid crystal-orientated, whereby the polymerizable liquid crystal compound and the liquid crystalline polymer compound can be orientated to form a liquid crystal phase.

When the formed coating film contains a liquid crystalline polymer compound and a polymerizable liquid crystal compound, the temperature at which the liquid crystalline polymer compound and the polymerizable liquid crystal compound are orientated only needs to be determined in advance by texture observation or the like using a composition containing the liquid crystalline polymer compound and the polymerizable liquid crystal compound. In addition, removal of the solvent and the liquid crystal orientation may be performed simultaneously. The temperature at this time depends on the kind of a solvent to be removed and the kind of a polymerizable liquid crystal compound, but is preferably in a range of 50° C. or higher and 200° C. or lower, and more preferably in a range of 80° C. or higher and 130° C. or lower when the substrate is a resin substrate.

(Step C)

When the formed coating film contains a polymerizable liquid crystal compound, the polymerizable liquid crystal compound is polymerized by irradiating the orientated polymerizable liquid crystal compound with an active energy ray.

By polymerizing the orientated polymerizable liquid crystal compound, a polarizing film containing the polymerizable liquid crystal compound polymerized in an orientated state and compound (1) orientated together with the polymerizable liquid crystal compound is obtained.

A polarizing film containing the polymerizable liquid crystal compound polymerized while the polymerizable liquid crystal compound maintains a smectic liquid crystal state has higher polarizing performance than a conventional host-guest type polarizing film, that is, a polarizing film obtained by polymerizing a polymerizable liquid crystal compound or the like while the polymerizable liquid crystal compound or the like maintains a nematic liquid crystal phase, and has better polarizing performance and strength than a polarizing film to which only a dichroic dye or a lyotropic liquid crystal type liquid crystal compound is applied.

An active energy ray source may be any source that generates an ultraviolet ray, an electron beam, an X-ray, or the like. The active energy ray source is preferably a light source having a light emission distribution at a wavelength of 400 nm or less, such as a low-pressure mercury lamp, a medium-pressure mercury lamp, a high-pressure mercury lamp, an ultra-high pressure mercury lamp, a chemical lamp, a black light lamp, a microwave-excited mercury lamp, or a metal halide lamp.

<Display Device>

The display device is a device having a display element, and is a device including a light emitting element or a light emitting device as a light emitting source. Examples of a display device including the film, preferably polarizing film according to the present embodiment include a liquid crystal display device, an organic electroluminescence (EL) display device, an inorganic electroluminescence (EL) display device, an electron emission display device (for example, a field emission display device (FED) or a surface field emission display device (SED)), an electronic paper (display device using electronic ink, electrophoresis element, and the like), a plasma display device, a projection-type display device (for example, a grating light valve (GLV) display device or a display device having a digital micromirror device (DMD)), and a piezoelectric ceramic display. The liquid crystal display device includes any of a transmissive liquid crystal display device, a semi-transmissive liquid crystal display device, a reflective liquid crystal display device, a direct view type liquid crystal display device, a projection type liquid crystal display device, and the like. These display devices may be display devices that display two-dimensional images or stereoscopic display devices that display three-dimensional images.

The film (preferably polarizing film) according to the present embodiment can be particularly effectively used for a liquid crystal display device, an organic electroluminescence (EL) display device, and an inorganic electroluminescence (EL) display device. The organic EL display device includes at least the film, preferably polarizing film according to the present embodiment, and an organic EL element. As the organic EL element, an element having a known configuration can be used.

A circularly polarizing plate which is a laminate including the film, preferably polarizing film according to the present embodiment, and a ¼ wavelength plate can be particularly effectively used for an organic electroluminescence (EL) display device and an inorganic electroluminescence (EL) display device. The organic EL display device includes at least the laminate, preferably circularly polarizing plate according to the present embodiment, and an organic EL element.

When the film, preferably polarizing film according to the present embodiment is used for a liquid crystal display device, the film may be disposed outside or inside a liquid crystal cell. The liquid crystal cell includes at least the film, preferably polarizing film according to the present embodiment, a liquid crystal layer, and a substrate.

EXAMPLES

Hereinafter, the present invention will be specifically described with reference to Examples, but the present invention is not limited to these Examples.

Example 1: Synthesis of Compound (2-2)

In order to synthesize compound (2-2), compound (2-2-a) was first synthesized. Subsequently, compound (2-2-a) and compound (2-1-c) were subjected to Suzuki coupling to obtain compound (2-2). Note that compound (2-1-c) was synthesized via compound (2-1-b).

Synthesis of Compound (2-2-a)

To a dichloromethane (60 mL) solution of EDC·HCl (abbreviation of 1-ethyl-3-(3-dimethylaminopropyl) carbodiimide hydrochloride, 1.21 g, 6.00 mmol) and DMAP (abbreviation of N,N-dimethylaminopyridine, 0.074 g, 0.60 mmol), n-hexanol (1.20 mL, 9.6 mmol) and 4-bromo-2,3,5,6-tetrafluorobenzoic acid (1.64 g, 6.00 mmol) were added in order. The mixture was stirred at room temperature for five hours. Thereafter, the reaction solution was washed with water and then with saturated saline, dried over magnesium sulfate, and concentrated with an evaporator to obtain compound (2-2-a) (1.69 g, yield 79%).

Synthesis of Compound (2-1-c)

A THF (450 mL) solution of compound (2-1-b) (18.3 g, 60.0 mmol) was cooled to −78° C. To the solution, a 1.57 M n-butyllithium hexane solution of (38.0 mL, 59.7 mmol) was added dropwise. Thereafter, the mixture was stirred for 30 minutes while the temperature was maintained at −78° C., and iPrOBpin (abbreviation of 2-isopropoxy-4,4,5,5-tetramethyl-1,3,2-dioxaborolane, 11.0 mL, 64.8 mmol) was further added dropwise thereto. After completion of the dropwise addition, the temperature was raised to normal temperature, and the mixture was stirred for 30 minutes. To the mixture, a water (400 mL) solution of ammonium chloride (60 g) was added to stop the reaction. The organic layer was separated, washed with saturated saline, then dried over magnesium sulfate, and concentrated with an evaporator. The obtained solid was purified by reprecipitation from chloroform/hexane to obtain compound (2-1-c) (16.7 g, yield 79%).

[Chemical formula 29]

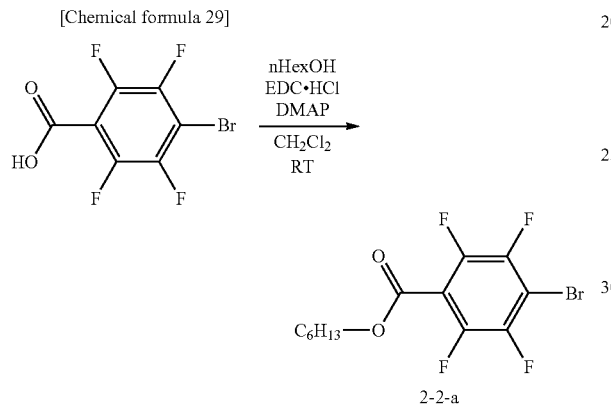

[Chemical formula 31]

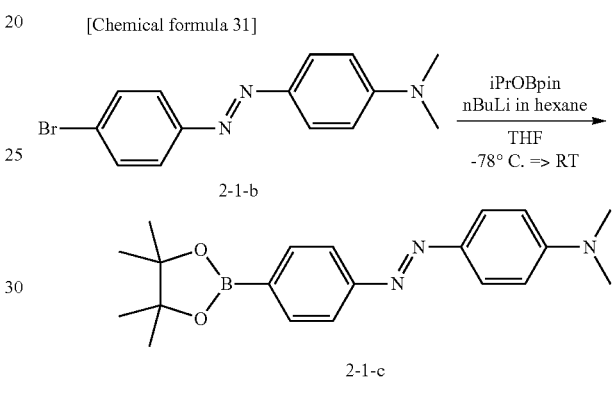

Synthesis of Compound (2-1-b)

4-Bromoaniline (13.2 g, 77.6 mmol), 35% hydrochloric acid (22.0 mL, 249 mmol), and water (200 mL) were mixed and cooled to a temperature of 0° C. to 5° C. To the mixture, a water (26 mL) solution of sodium nitrite (13.0 g, 189 mmol) was added dropwise. Thereafter, the mixture was stirred for 30 minutes while the temperature was maintained at 0° C. to 5° C., and amide sulfuric acid (11.0 g, 113 mmol) was further added thereto to prepare a diazo liquid. Meanwhile, N,N-dimethylaniline (14.0 mL, 111 mmol), sodium acetate (24.8 g, 302 mmol), methanol (200 mL), and water (100 mL) were mixed and cooled to a temperature of 0° C. to 5° C. To the mixture, the whole amount of the diazo liquid prepared above was added dropwise. After completion of the dropwise addition, the temperature was raised to normal temperature, and the precipitated solid was separated by filtration to obtain compound (2-1-b) (21.0 g, yield 90%).

Synthesis of Compound (2-2)

To a THF (10 mL) solution of compound (2-2-a) (396 mg, 1.11 mmol) and compound (2-1-c) (351 mg, 1.00 mmol), Pd$_2$dba$_3$ (22.9 mg, 0.025 mmol) and P(t-Bu)$_3$·HBF$_4$ (14.4 mg, 0.050 mmol) were added, and the mixture was stirred. To the mixture, a 3 M potassium phosphate aqueous solution (1.0 mL, 3.0 mmol) was further added, and the mixture was refluxed and stirred for nine hours. To the reaction solution, THF was added, and the mixture was caused to pass through a silica gel short column and then concentrated with an evaporator. The obtained solid was purified by silica gel column chromatography (chloroform/toluene=20/80). The purified product was further purified by preparative GPC to obtain compound (2-2) (88 mg, yield 18%).

$^1$H-NMR (400 MHz, CDCl$_3$): δ (ppm)=7.97-7.89 (m, 4H), 7.60-7.57 (m, 2H), 6.79-6.76 (m, 2H), 4.42 (t, 2H), 3.11 (s, 6H), 1.78 (tt, 2H), 1.49-1.42 (m, 2H), 1.38-1.33 (m, 4H), 0.91 (t, 3H).

[Chemical formula 30]

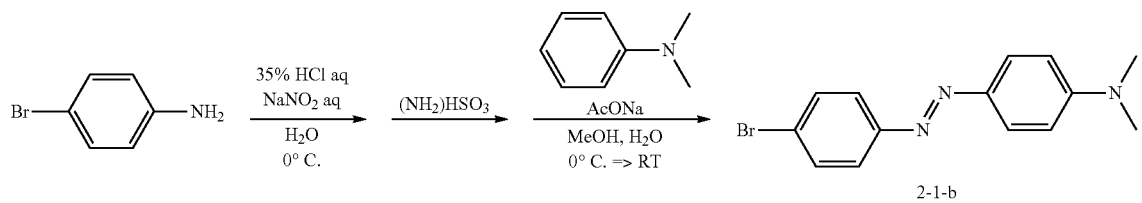

[Chemical formula 32]

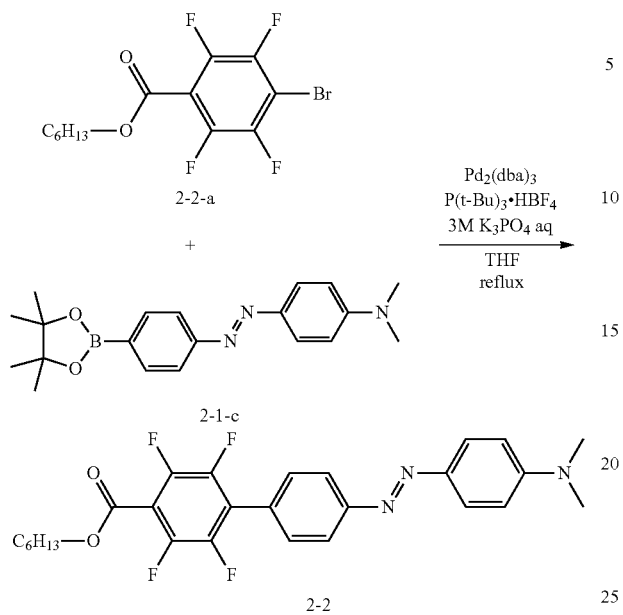

Example 2: Synthesis of Compound (2-3)

In order to synthesize compound (2-3), compound (2-3-a) was first synthesized. Subsequently, compound (2-3-a) and the above-described compound (2-1-c) were subjected to Suzuki coupling to obtain compound (2-3).

Synthesis of Compound (2-3-a)

To a chloroform (80 mL) solution of EDC·HCl (1.61 g, 8.41 mmol) and DMAP (0.098 g, 0.80 mmol), ethanol (1.85 g, 40.1 mmol) and 4-bromo-2,6-difluorobenzoic acid (1.90 g, 8.01 mmol) were added in order. The mixture was stirred at room temperature for four hours. Thereafter, the reaction solution was washed with water and then with saturated saline, dried over magnesium sulfate, and concentrated with an evaporator. The concentrated product was dissolved in a mixed solvent of chloroform/hexane=1/1, caused to pass through a silica gel short column, and then concentrated with an evaporator to obtain compound (2-3-a) (1.32 g, yield 62%).

[Chemical formula 33]

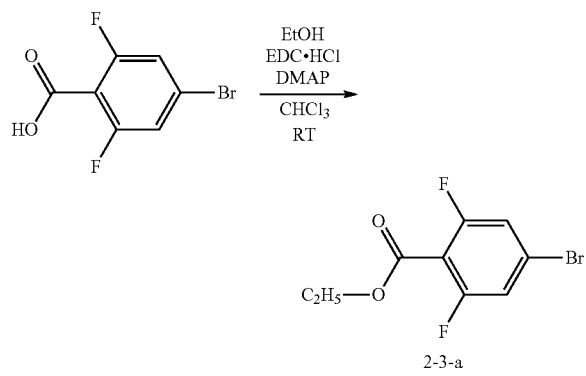

Synthesis of Compound (2-3)

To a THF (10 mL) solution of compound (2-3-a) (292 mg, 1.10 mmol) and compound (2-1-c) (351 mg, 1.00 mmol), $Pd_2(dba)_3$ (22.7 mg, 0.0248 mmol) and $P(t-Bu)_3·HBF_4$ (15.2 mg, 0.0524 mmol) were added, and the mixture was stirred. To the mixture, a 3 M potassium phosphate aqueous solution (1.0 mL, 3.0 mmol) was further added, and the mixture was heated and stirred at 60° C. for 4.5 hours. To the reaction solution, methanol (20 mL) was added, and the precipitated solid was collected by filtration and purified by silica gel column chromatography using chloroform as an eluent to obtain compound (2-3) (161 mg, yield 39'%).

$^1$H-NMR (400 MHz, $CDCl_3$): δ (ppm)=7.95-7.89 (m, 4H), 7.69-7.66 (m, 2H), 7.26-7.22 (m, 2H), 6.79-6.75 (m, 2H), 4.45 (q, 2H), 3.11 (s, 6H), 1.42 (t, 3H).

[Chemical formula 34]

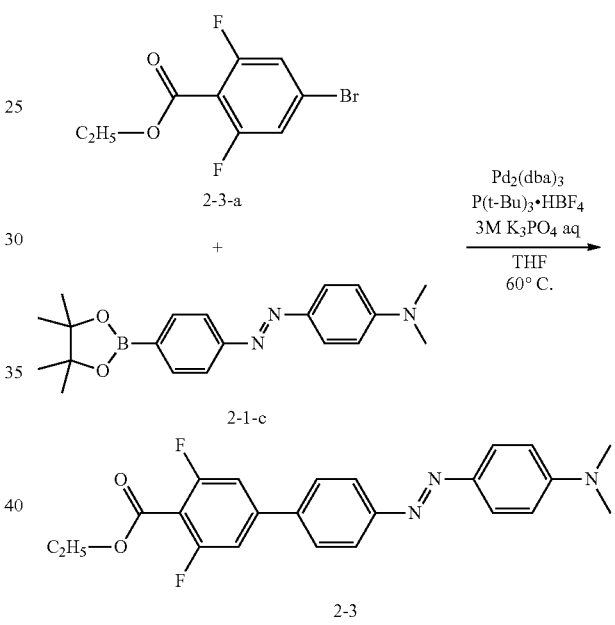

Example 3: Synthesis of Compound (2-4)

In order to synthesize compound (2-4), compound (2-4-a) was first synthesized. Subsequently, compound (2-4-a) and the above-described compound (2-1-c) were subjected to Suzuki coupling to obtain compound (2-4).

Synthesis of Compound (2-4-a)

To a chloroform (80 mL) solution of EDC·HCl (1.61 g, 8.41 mmol) and DMAP (0.098 g, 0.80 mmol), ethanol (1.84 g, 40.0 mmol) and 4-bromo-2-fluorobenzoic acid (1.75 g, 8.00 mmol) were added in order. The mixture was stirred at room temperature for 3.5 hours. Thereafter, the reaction solution was washed with water and then with saturated saline. The washed product was dried over magnesium sulfate and concentrated with an evaporator to obtain compound (2-4-a) (1.60 g, yield 81%).

[Chemical formula 35]

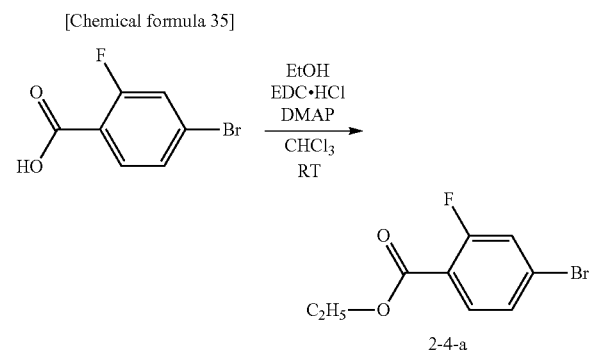

Synthesis of Compound (2-4)

To a THF (10 mL) solution of compound (2-4-a) (552 mg, 2.23 mmol) and compound (2-1-c) (704 mg, 2.01 mmol), $Pd_2(dba)_3$ (46.1 mg, 0.0503 mmol) and $P(t-Bu)_3 \cdot HBF_4$ (29.0 mg, 0.100 mmol) were added, and the mixture was stirred. To the mixture, a 3 M potassium phosphate aqueous solution (2.0 mL, 6.0 mmol) was further added, and the mixture was heated and stirred at 60° C. for 3.5 hours. To the reaction solution, water (20 mL) was added, and the precipitated solid was collected by filtration and purified by silica gel column chromatography using chloroform as an eluent to obtain compound (2-4) (480 mg, yield 61%).

$^1$H-NMR (400 MHz, $CDCl_3$): δ (ppm)=8.02 (dd, 1H), 7.95-7.89 (m, 4H), 7.74-7.70 (m, 2H), 7.50 (dd, 1H), 7.43 (dd, 1H), 6.80-6.76 (m, 2H), 4.43 (q, 2H), 3.11 (s, 6H), 1.43 (t, 3H).

[Chemical formula 36]

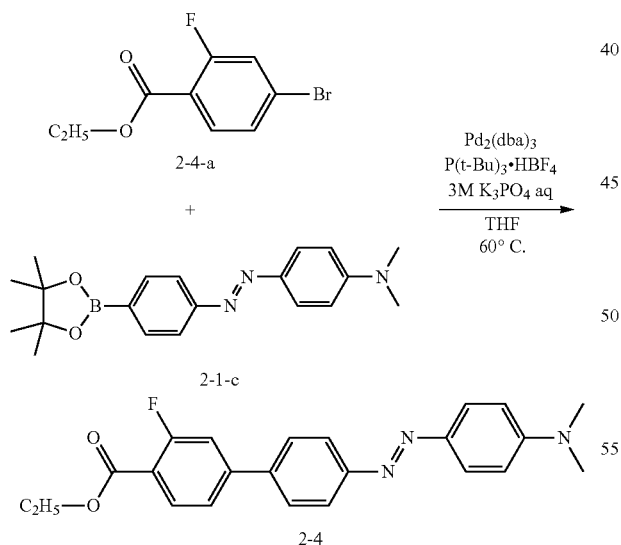

Example 4: Synthesis of Compound (2-5)

In order to synthesize compound (2-5), compound (2-5-b) was first synthesized via compound (2-5-a). Subsequently, compound (2-5-b) and ethyl 4-bromobenzoate were subjected to Suzuki coupling to obtain compound (2-5).

Synthesis of Compound (2-5-a)

4-Bromo-2-fluoroaniline (14.3 g, 75.0 mmol), 35% hydrochloric acid (22.0 mL, 249 mmol), and water (200 mL) were mixed and cooled to a temperature of 0° C. to 5° C. To the mixture, a water (26 mL) solution of sodium nitrite (7.76 g, 112 mmol) was added dropwise. Thereafter, the mixture was stirred for 30 minutes while the temperature was maintained at 0° C. to 5° C., and amide sulfuric acid (4.36 g, 45.0 mmol) was further added thereto to prepare a diazo liquid. Meanwhile, dimethylaniline (13.6 g, 113 mmol), sodium acetate (24.6 g, 300 mmol), methanol (200 mL), and water (100 mL) were mixed and cooled to a temperature of 0° C. to 5° C. To the mixture, the whole amount of the diazo liquid prepared above was added dropwise. After completion of the dropwise addition, the temperature was raised to normal temperature, and the precipitated solid was separated by filtration to obtain compound (2-5-a) (15.8 g, yield 66%).

[Chemical formula 37]

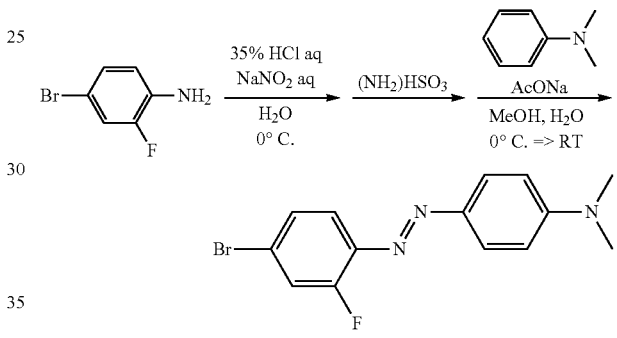

Synthesis of Compound (2-5-b)

To a 1,4-dioxane (60 mL) solution of compound (2-5-a) (3.23 g, 10.0 mmol), $B_2pin_2$ (bis(pinacolato) diboron, 2.79 g, 11.0 mmol), and potassium acetate (2.99 g, 30.4 mmol), $PdCl_2dppf$ (249 mg, 0.305 mmol) was added, and the mixture was heated and stirred at 80° C. for seven hours. The reaction solution was separated with toluene/water, and the organic layer was washed with water and then with saturated saline, then dried over magnesium sulfate, and concentrated with an evaporator. The obtained solid was purified by reprecipitation from chloroform/hexane to obtain compound (2-5-b) (2.53 g, yield 69%).

[Chemical formula 38]

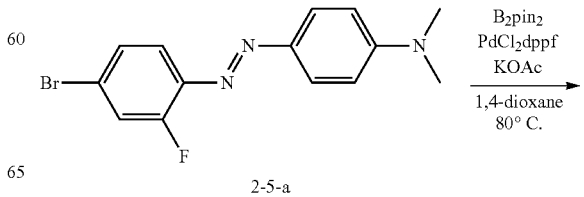

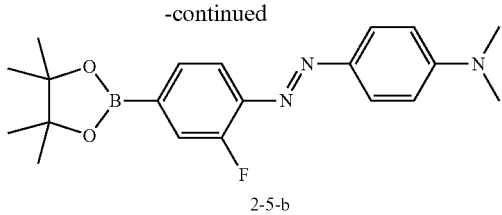

2-5-b

Synthesis of Compound (2-5)

To a THF (30 mL) solution of ethyl 4-bromobenzoate (0.763 g, 3.33 mmol) and compound (2-5-b) (1.11 g, 3.00 mmol), $Pd_2(dba)_3$ (69.8 mg, 0.0762 mmol) and $P(t\text{-}Bu)_3 \cdot HBF_4$ (45.0 mg, 0.155 mmol) were added, and the mixture was stirred. To the mixture, a 3 M potassium phosphate aqueous solution (4.0 mL, 12.0 mmol) was further added, and the mixture was heated and stirred at 60° C. for four hours. To the reaction solution, methanol (20 mL) was added, and the precipitated solid was collected by filtration and purified by silica gel column chromatography using chloroform as an eluent to obtain compound (2-5) (904 mg, yield 771).

$^1$H-NMR (400 MHz, $CDCl_3$): δ (ppm)=8.15-8.12 (m, 2H), 7.95-7.91 (m, 2H), 7.84 (d, 1H), 7.72-7.68 (m, 2H), 7.52-7.45 (m, 2H), 6.79-6.75 (m, 2H), 4.42 (q, 2H), 3.12 (s, 6H), 1.43 (t, 3H).

[Chemical formula 39]

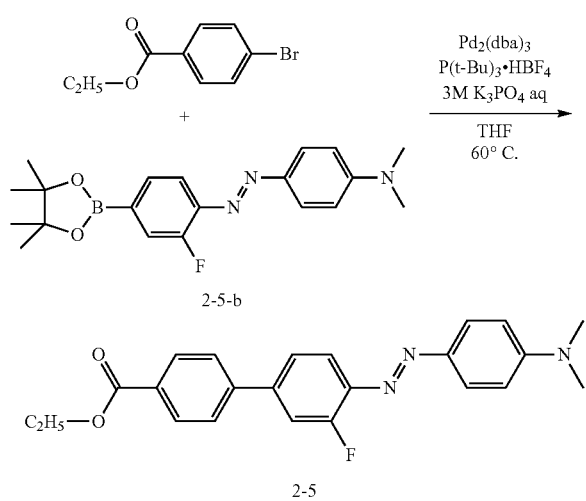

Example 5: Synthesis of Compound (2-7)

In order to synthesize compound (2-7), compound (2-6-a) was first synthesized via the above-described compound (2-5-a). Subsequently, compound (2-6-a) and 4-n-octyloxybenzoic acid were subjected to dehydration condensation to obtain compound (2-7).

Synthesis of Compound (2-6-a)

To a 1,4 dioxane (7.5 mL) and water (7.5 mL) mixed solution of compound (2-5-a) (1.61 g, 5.00 mmol) and potassium hydroxide (0.83 g, 15 mmol), $Pd_2(dba)_3$ (91.6 mg, 0.100 mmol) and t-BuXPhos (170 mg, 0.401 mmol) were added, and the mixture was heated and stirred at 100° C. for 1.5 hours. To the reaction solution, acetic acid (1 mL) was added to stop the reaction. The mixture was separated with ethyl acetate/water. The organic layer was washed with water and then with saturated saline, then dried over magnesium sulfate, and concentrated with an evaporator. The obtained solid was purified by silica gel column chromatography (ethyl acetate/chloroform=10/90) to obtain compound (2-6-a). (1.02 g, yield 79%).

[Chemical formula 40]

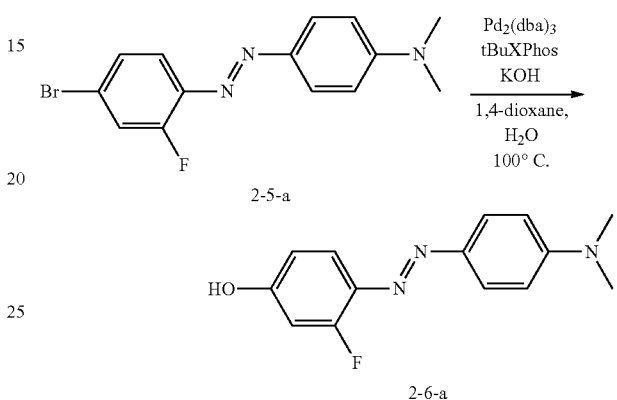

Synthesis of Compound (2-7)

To a chloroform (10 mL) solution of EDC·HCl (207 mg, 1.05 mmol) and DMAP (13.4 mg, 0.10 mmol), compound (2-6-a) (0.260 g, 1.00 mmol) and 4-n-octyloxybenzoic acid (0.251 g, 1.00 mmol) were added in order. The mixture was stirred at room temperature for six hours. Thereafter, the reaction solution was washed with water and then with saturated saline, dried over magnesium sulfate, and concentrated with an evaporator. The obtained solid was purified by recrystallization (chloroform/methanol) to obtain compound (2-7) (379 mg, yield 77%).

$^1$H-NMR (400 MHz, $CDCl_3$): δ (ppm)=8.15-8.11 (m, 2H), 7.92-7.88 (m, 2H), 7.81 (dd, 1H), 7.16 (dd, 2H), 7.07-7.04 (m, 2H), 6.99-6.95 (m, 2H), 6.76-6.72 (m, 2H), 4.04 (t, 2H), 3.09 (s, 6H), 1.82 (tt, 2H), 1.51-1.43 (m, 2H), 1.40-1.24 (m, 8H), 0.89 (t, 3H).

[Chemical formula 41]

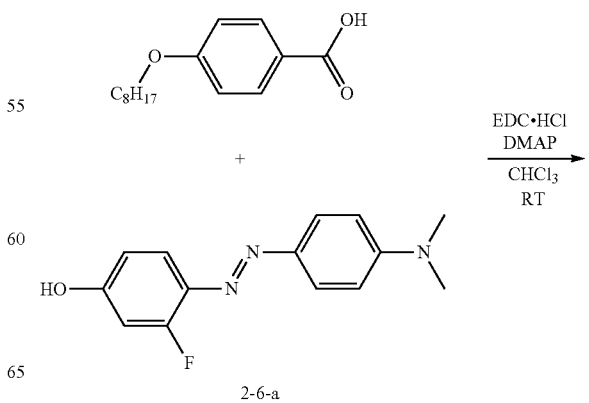

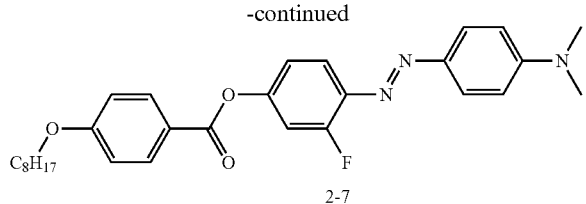

2-7

Example 6: Synthesis of Compound (2-101)

In order to synthesize compound (2-101), compound (2-101-a) was first synthesized.

Subsequently, compound (2-101-a) and the above-described compound (2-5-b) were subjected to Suzuki coupling to obtain compound (2-101-b). Subsequently, compound (2-101-b) was subjected to a transesterification reaction to obtain compound (2-101).

Synthesis of Compound (2-101-a)

To an acetonitrile (200 mL) solution of copper (II) bromide (6.48 g, 29.0 mmol), isobutyl nitrite (4.40 mL, 37 mmol) and ethyl 2-aminobenzothiazole-6 carboxylate (5.56 g, 25.0 mmol) were added in order. The mixture was stirred at 65° C. for 1.5 hours. Thereafter, the reaction solution was cooled to room temperature, and then poured into 0.4 M hydrochloric acid (200 mL) to stop the reaction. The reaction solution was separated with chloroform/water. Thereafter, the organic layer was washed with water and then with saturated saline, dried over magnesium sulfate, and concentrated with an evaporator to obtain compound (2-101-a) (6.56 g, yield 92%).

[Chemical formula 42]

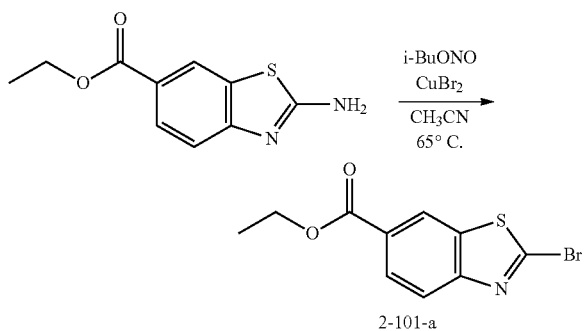

Synthesis of Compound (2-101-b)

To a THF (20 mL) solution of compound (2-101-a) (0.631 g, 2.21 mmol) and compound (2-5-b) (0.739 g, 2.00 mmol), $Pd_2(dba)_3$ (0.0464 g, 0.0507 mmol) and $P(t-Bu)_3 \cdot HBF_4$ (0.0290 g, 0.100 mmol) were added, and the mixture was stirred. To the mixture, a 3 M potassium phosphate aqueous solution (2.0 mL, 6.0 mmol) was further added, and the mixture was heated and stirred at 60° C. for 12 hours. To the reaction solution, methanol was added, and the precipitated solid was collected by filtration to obtain compound (2-101-b) (0.782 g, yield 87%).

[Chemical formula 43]

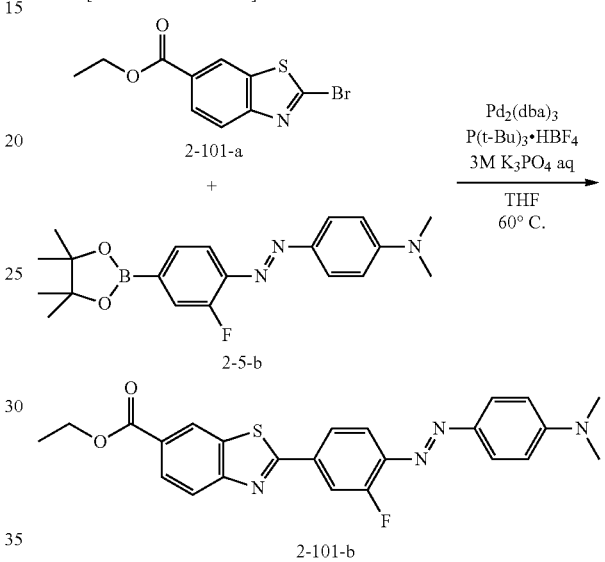

Synthesis of Compound (2-101)

A p-xylene (15 mL) solution of compound (2-101-b) (0.450 g, 1.00 mmol), $TiO(acac)_2$ (abbreviation of bis(2,4-pentanedionato) titanium (IV) oxide, 0.132 g, 0.504 mmol), and n-hexanol (0.512 g, 5.01 mmol) was heated and refluxed for four hours. To the reaction solution, methanol was added, and the precipitated solid was collected by filtration and purified by silica gel column chromatography using chloroform as an eluent to obtain compound (2-101) (0.366 g, yield 72%).

$^1$H-NMR (400 MHz, $CDCl_3$): δ (ppm)=8.65 (d, 1H), 8.19 (dd, 1H), 8.11 (d, 1H), 8.02 (dd, 1H), 7.97-7.91 (m, 3H), 7.88 (dd, 1H), 6.79-6.75 (m, 2H), 4.38 (t, 2H), 3.13 (s, 6H), 1.82 (tt, 2H), 1.52-1.45 (m, 2H), 1.40-1.34 (m, 4H), 0.92 (t, 3H).

[Chemical formula 44]

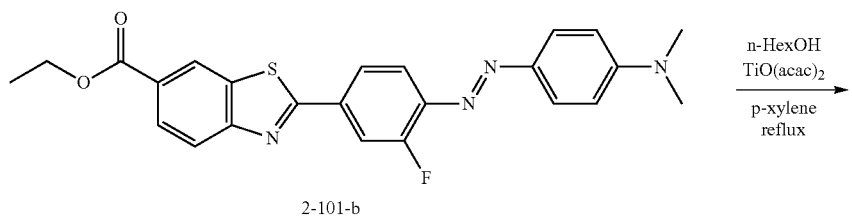

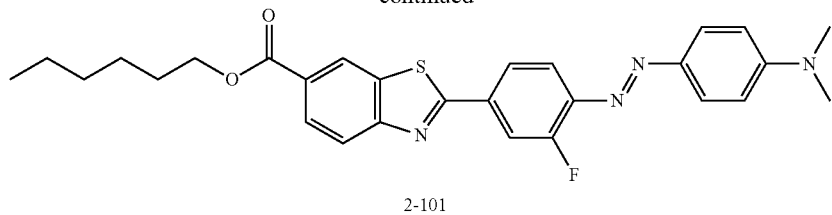

2-101

Example 7: Synthesis of Compound (2-76)

2-Bromo-5-n-butylthienothiazole and the above-described compound (2-5-b) were subjected to Suzuki coupling to obtain compound (2-76).

Synthesis of Compound (2-76)

To a THF (10 mL) solution of 2-bromo-5-n-butylthienothiazole (0.304 g, 1.10 mmol) and compound (2-5-b) (0.369 g, 1.00 mmol), $Pd_2(dba)_3$ (0.0367 mg, 0.0400 mmol) and $P(t\text{-}Bu)_3 \cdot HBF_4$ (0.0232 mg, 0.0800 mmol) were added, and the mixture was stirred.

To the mixture, a 3 M potassium phosphate aqueous solution (2.0 mL, 6.0 mmol) was further added, and the mixture was heated and stirred for 16 hours. To the reaction solution, methanol was added, and the precipitated solid was collected by filtration and purified by silica gel column chromatography (chloroform/toluene=10/90) to obtain compound (2-76) (0.127 g, yield 29%).

$^1$H-NMR (400 MHz, $CDCl_3$): δ (ppm)=9.95-7.91 (m, 2H), 7.87-7.81 (m, 2H), 7.77 (dd, 1H), 6.95 (s, 1H), 6.78-6.74 (m, 2H), 3.12 (s, 6H), 2.92 (t, 2H), 1.74 (tt, 2H), 1.44 (tq, 2H), 0.97 (t, 3H).

Example 8: Synthesis of Compound (2-102)

In order to synthesize compound (2-102), compound (2-102-b) was first synthesized via the above-described compound (2-101-a) and compound (2-102-a). Subsequently, compound (2-102-d) was synthesized via compound (2-102-c). Compound (2-102-b) and compound (2-102-d) were subjected to Suzuki coupling to obtain compound (2-102).

Synthesis of Compound (2-102-a)

Compound (2-101-a) (10.3 g, 36.0 mmol), lithium hydroxide monohydrate (7.55 g, 180 mmol), and THF (360 mL) were mixed, and the mixture was cooled to a temperature of 0° C. to 5° C. To the mixture, water (120 mL) was added, and the temperature was raised to normal temperature. The mixture was stirred at room temperature for three days, and then poured into 1 M hydrochloric acid (200 mL) to stop the reaction. The reaction solution was separated with ethyl acetate/water. Thereafter, the organic layer was washed with water and then with saturated saline, dried over magnesium sulfate, and concentrated with an evaporator to obtain compound (2-102-a) (9.02 g, yield 97%).

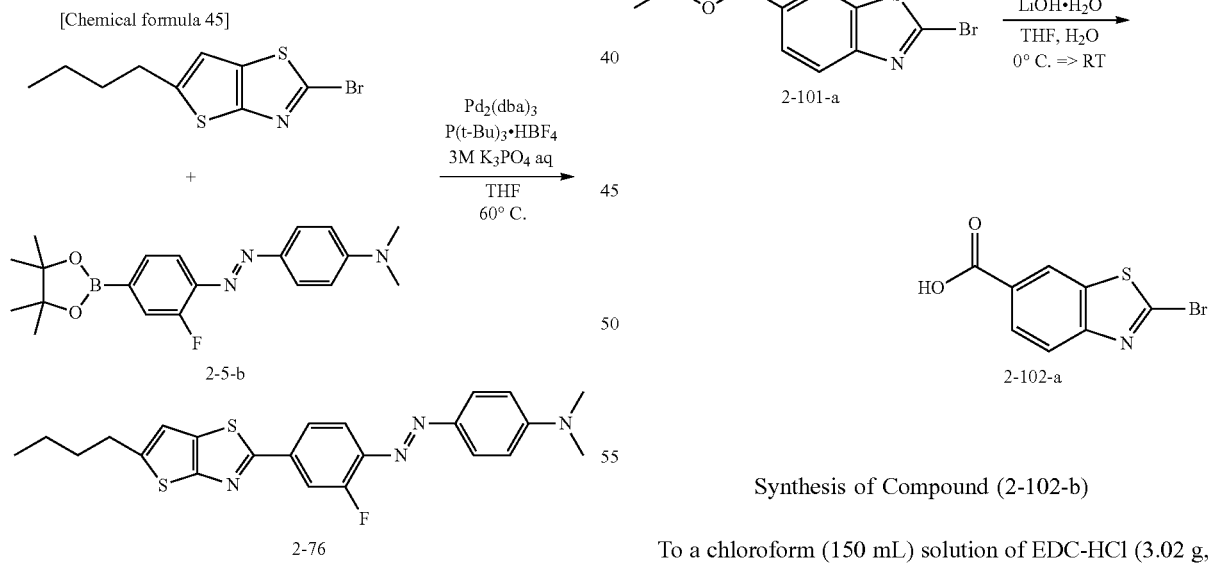

Synthesis of Compound (2-102-b)

To a chloroform (150 mL) solution of EDC-HCl (3.02 g, 15.8 mmol) and DMAP (184 mg, 1.50 mmol), n-hexanol (1.61 g, 15.7 mmol) and compound (2-102-a) (3.87 g, 15.0 mmol) were added in order. The mixture was stirred at room temperature for 7.5 hours. Thereafter, the reaction solution was washed with water and then with saturated saline, dried over magnesium sulfate, caused to pass through a silica gel short column, and concentrated with an evaporator to obtain compound (2-102-b) (4.44 g, yield 87%).

65

[Chemical formula 47]

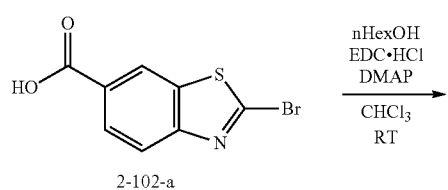

Synthesis of Compound (2-102-c)

4-Bromo-3-fluoroaniline (1.90 g, 10.0 mmol), 35% hydrochloric acid (3.0 mL, 34 mmol), and water (25 mL) were mixed and cooled to a temperature of 0° C. to 5° C. To the mixture, a water (2.5 mL) solution of sodium nitrite (0.69 mg, 10.0 mmol) was added dropwise to prepare a diazo liquid. Meanwhile, dimethylaniline (1.33 g, 11.0 mmol), sodium acetate (3.28 g, 40.0 mmol), methanol (25.0 mL), and water (12.5 mL) were mixed and cooled to a temperature of 0° C. to 5° C. To the mixture, the whole amount of the diazo liquid prepared above was added dropwise. After completion of the dropwise addition, the temperature was raised to normal temperature, and the precipitated solid was separated by filtration to obtain compound (2-102-c) (2.59 g, yield 80%).

[Chemical formula 48]

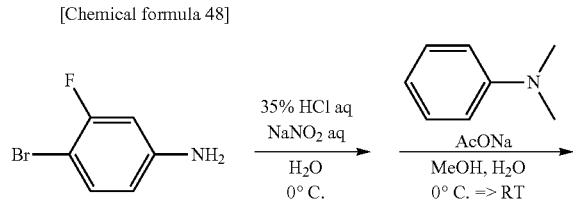

66

Synthesis of Compound (2-102-d)

To a 1,4-dioxane (35 mL) solution of compound (2-102-c) (2.26 g, 7.00 mmol), B₂pin₂ (official name is bis(pinacolato)diboron, 1.96 g, 7.70 mmol), and potassium acetate (2.06 g, 21.0 mmol), PdCl₂dppf (0.286 g, 0.351 mmol) was added, and the mixture was heated and stirred at 80° C. for 15 hours. The reaction solution was separated with toluene/water, and the organic layer was washed with water and then with saturated saline, then dried over magnesium sulfate, and concentrated with an evaporator. The obtained solid was purified by reprecipitation from chloroform/hexane to obtain compound (2-102-d) (1.74 g, yield 67%).

[Chemical formula 49]

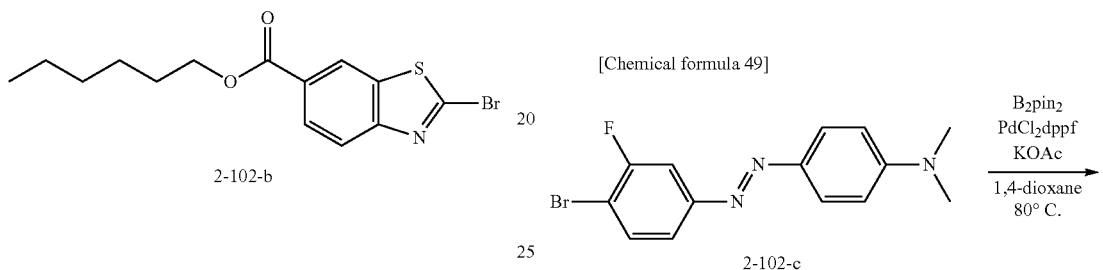

Synthesis of Compound (2-102)

To a 1,4-dioxane (10 mL) solution of compound (2-102-b) (0.378 g, 1.10 mmol) and compound (2-102-d) (0.369 g, 1.00 mmol), Pd₂(dba)₃ (0.0231 g, 0.0252 mmol) and P(t-Bu)₃·HBF₄ (0.0145 g, 0.0500 mmol) were added, and the mixture was stirred. To the mixture, a 3 M potassium phosphate aqueous solution (1.0 mL, 3.0 mmol) was further added, and the mixture was heated and stirred at 100° C. for three hours. To the reaction solution, methanol was added, and the precipitated solid was collected by filtration and purified by silica gel column chromatography using chloroform as an eluent, and further purified by reprecipitation from chloroform/methanol to obtain compound (2-102) (0.356 g, yield 71%).

¹H-NMR (400 MHz, CDCl₃): δ (ppm)=8.68 (d, 1H), 8.57 (dd, 1H), 8.20 (dd, 1H), 8.14 (d, 1H), 7.95-7.91 (m, 2H), 7.83 (dd, 1H), 7.72 (dd, 1H), 6.80-6.76 (m, 2H), 4.38 (t, 2H), 3.14 (s, 6H), 1.82 (tt, 2H), 1.52-1.45 (m, 2H), 1.40-1.34 (m, 4H), 0.92 (t, 3H).

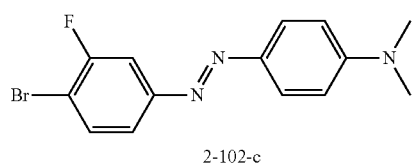

[Chemical formula 50]

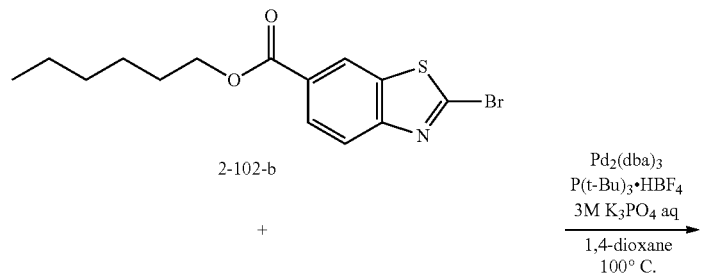

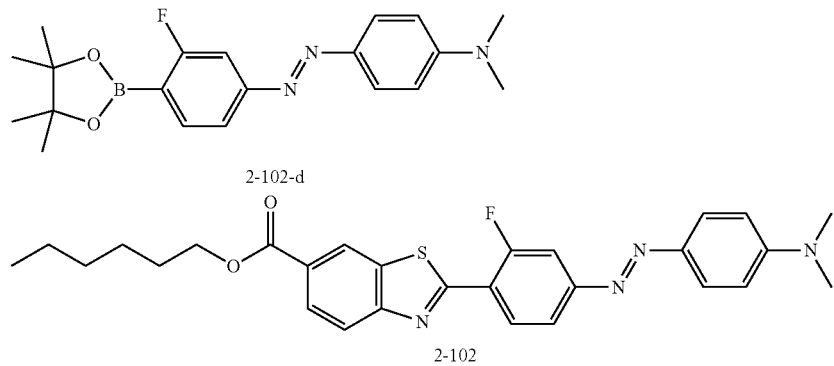

Example 9: Synthesis of Compound (2-77)

2-Bromo-5-n-butylthienothiazole and the above-described compound (2-102-d) were subjected to Suzuki coupling to obtain compound (2-77).

Synthesis of Compound (2-77)

To a 1,4-dioxane (10 mL) solution of 2-bromo-5-n-butylthienothiazole (0.307 g, 1.11 mmol) and compound (2-102-d) (0.370 g, 1.00 mmol), $Pd_2(dba)_3$ (0.023 g, 0.0251 mmol) and $P(t-Bu)_3 \cdot HBF_4$ (0.015 g, 0.0517 mmol) were added, and the mixture was stirred. To the mixture, a 3 M potassium phosphate aqueous solution (1.0 mL, 3.0 mmol) was further added, and the mixture was heated and stirred for four hours. To the reaction solution, methanol was added, and the precipitated solid was collected by filtration and purified by silica gel column chromatography using chloroform as an eluent, and further purified by reprecipitation from chloroform/methanol to obtain compound (2-77) (0.317 g, yield 72%).

$^1$H-NMR (400 MHz, $CDCl_3$): δ (ppm)=8.42 (dd, 1H), 7.92-7.89 (m, 2H), 7.78 (dd, 1H), 7.68 (dd, 1H), 6.97 (s, 1H), 6.79-6.75 (m, 2H), 3.12 (s, 6H), 2.93 (t, 2H), 1.75 (tt, 2H), 1.45 (tq, 2H), 0.97 (t, 3H).

[Chemical formula 51]

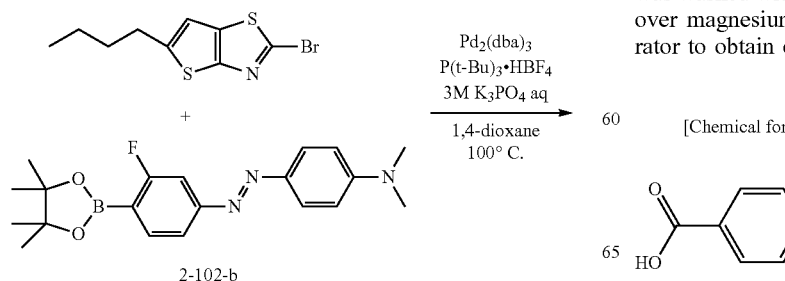

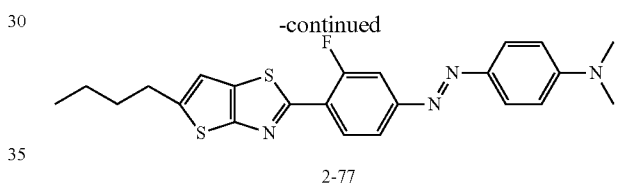

Comparative Example 1: Synthesis of Compound (2-1)

In order to synthesize compound (2-1), compound (2-1-a) was first synthesized. Subsequently, compound (2-1-a) and the above-described compound (2-1-c) were subjected to Suzuki coupling to obtain compound (2-1).

Synthesis of Compound (2-1-a)

To a dichloromethane (60 mL) solution of $EDC \cdot HCl$ (1.36 g, 7.10 mmol) and DMAP (0.083 g, 0.68 mmol), n-hexanol (0.90 mL, 7.2 mmol) and 4-bromobenzoic acid (1.36 g, 6.76 mmol) were added in order. The mixture was stirred at room temperature for six hours. Thereafter, the reaction solution was washed with water and then with saturated saline, dried over magnesium sulfate, and concentrated with an evaporator to obtain compound (2-1-a) (1.70 g, yield 88%).

[Chemical formula 52]

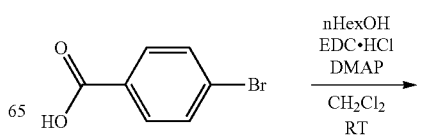

-continued

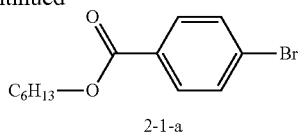

2-1-a

Synthesis of Compound (2-1)

To a diethylene glycol dimethyl ether (13 mL) and water (2 mL) mixed solution of compound (2-1-a) (285 mg, 1.00 mmol), compound (2-1-c) (457 mg, 1.30 mmol), potassium acetate (650 mg, 6.63 mmol), PdCl$_2$dppf (41.0 mg, 0.0502 mmol) was added, and the mixture was heated and stirred at 140° C. for four hours. To the reaction solution, THF was added, and the mixture was caused to pass through a silica gel short column and then concentrated with an evaporator. The obtained solid was washed with methanol/water and then purified by silica gel column chromatography (chloroform/toluene=20/80) to obtain compound (2-1) (238 mg, yield 55%).

$^1$H-NMR (400 MHz, CDCl$_3$): δ (ppm)=8.14-8.11 (m, 2H), 7.95-7.89 (m, 4H), 7.76-7.71 (m, 4H), 6.80-6.76 (m, 2H), 4.35 (t, 2H), 3.11 (s, 6H), 1.79 (tt, 2H), 1.51-1.44 (m, 2H), 1.37-1.33 (m, 4H), 0.92 (t, 3H).

[Chemical formula 53]

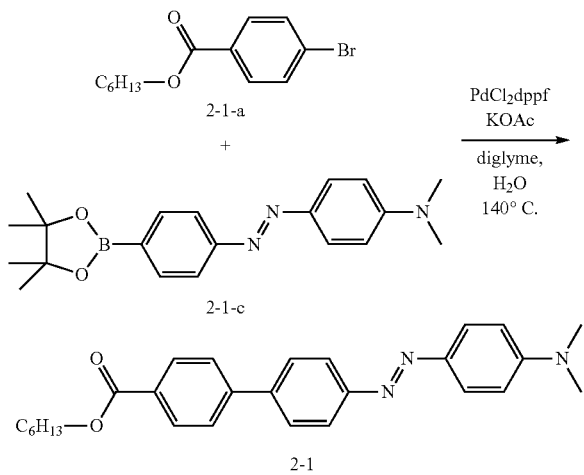

<Evaluation>

Preparation of Composition 1 g of a 10% by mass poly (methyl methacrylate) (PMMA, manufactured by Aldrich, Mw=about 120,000) toluene aqueous solution, 4 mg of compound (2-2) obtained in Example 1, and 6 mg of a photoradical initiator (IRGACURE 369) were mixed, and the mixture was heated at 80° C. for 30 minutes to prepare composition E1.

Compositions E2 to E9 and composition C1 were obtained in a similar manner to the above except that compounds (2-3) to (2-5), compound (2-7), compound (2-101), compound (2-76), compound (2-102), compound (2-77), or compound (2-1) were used instead of compound (2-2).

Formation of Thin Film

A glass substrate was used as a transparent substrate. Composition E1 was spin-coated on a glass substrate using a spin coater (MS-A100, rotation speed 1000 rpm, 20 seconds) to form a thin film, thus obtaining a laminate for evaluation.

Thin films were formed in a similar manner to the above except that compositions E2 to E9 and composition C1 were used instead of composition E1, thus obtaining laminates for evaluation.

Absorbance Measurement

For each of the laminates for evaluation obtained above, a UV-vis spectrum was measured at normal temperature (25° C.) using a spectrophotometer (CARY UV-vis-NIR Spectrophotometer 5E manufactured by Varian, Inc.) to obtain absorbance (abs$_1$) at a maximum absorption wavelength ($\lambda_{max1}$) and a maximum absorption wavelength ($\lambda_{max1}$). Thereafter, each of the laminates for evaluation was irradiated with UV light of 3000 mJ/cm$^2$ at 25° C. using an exposure machine (MA-1300A type manufactured by NIPPON KAKEN CO., LTD.). Thereafter, a UV-vis spectrum was measured again to obtain absorbance (abs$_2$) at a maximum absorption wavelength ($\lambda_{max2}$) and a maximum absorption wavelength ($\lambda_{max2}$) after UV irradiation.

An absorbance retention ratio (%) was calculated by dividing the absorbance after UV irradiation (abs$_2$) by the absorbance before UV irradiation (abs$_1$). Results thereof are indicated in Table 1. When the absorbance retention ratio of a laminate exceeds 80%, the laminate is regarded as a favorable polarizing plate.

TABLE 1

|  | Compound | Before UV irradiation | | After UV irradiation | | Absorbance retention ratio (%) |
|---|---|---|---|---|---|---|
|  |  | Absorbance (abs$_1$) | $\lambda_{max1}$ (nm) | Absorbance (abs$_2$) | $\lambda max2$ (nm) |  |
| Example 1 | 2-2 | 0.184 | 439 | 0.157 | 439 | 85. |
| Example 2 | 2-3 | 0.204 | 443 | 0.81 | 443 | 88.7 |
| Example 3 | 2-4 | 0.172 | 442 | 0.164 | 442 | 95.4 |
| Example 4 | 2-5 | 0.192 | 460 | 0.179 | 460 | 93.2 |
| Example 5 | 2-7 | 0.16 | 432 | 0.135 | 432 | 84.4 |
| Example 6 | 2-101 | 0.458 | 485 | 0.409 | 484 | 89.3 |
| Example 7 | 2-76 | 0.398 | 480 | 0.324 | 478 | 81.4 |
| Example 8 | 2-102 | 0.75 | 481 | 0.688 | 482 | 91.7 |
| Example 9 | 2-77 | 0.716 | 476 | 0.659 | 476 | 92 |
| Comparative Example 1 | 2-1 | 0.204 | 436 | 0.16 | 436 | 78.4 |

Table 1 indicates that the compound represented by formula (1) has high ultraviolet (UV) durability.

The invention claimed is:

1. A compound represented by the following formula (1):

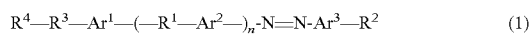
(1)

wherein $Ar^1$, $Ar^2$, and $Ar^3$ each independently represent a 1,4-phenylene group optionally having a substituent or a divalent sulfur-containing aromatic heterocyclic group optionally having a substituent, and at least one of $Ar^1$ and $Ar^2$ has a fluorine atom as a substituent;

n is an integer of 1 or 2;

$R^1$ represents a single bond or at least one group selected from the group consisting of —OC(=O)—, —C(=O)O—, —C≡C—, —CH=CH—, —CH=N—, and —N=CH—;

$R^2$ represents an alkylamino group optionally having a polymerizable group;

$R^3$ represents at least one group selected from the group consisting of an alkanediyl group having 4 to 20 carbon atoms, an alkanediyloxy group having 2 to 20 carbon atoms, an alkanediyloxycarbonyl group having 2 to 20 carbon atoms, and an alkanediylcarbonyloxy group having 2 to 20 carbon atoms;

$R^4$ represents a polymerizable group or a hydrogen atom;

when n is 2, two $R^1$s may be the same as or different from each other, and two $Ar^2$s may be the same as or different from each other.

2. The compound according to claim 1, wherein either one of $Ar^1$ and $Ar^2$ has one or two fluorine atoms as a substituent in the formula (1).

3. The compound according to claim 1, wherein $R^1$ is a single bond in the formula (1).

4. The compound according to claim 1, wherein n is an integer of 1 in the formula (1).

5. The compound according to claim 1, wherein the polymerizable group is a radically polymerizable group.

6. A composition comprising the compound according to claim 1.

7. A film comprising the compound according to claim 1 as a forming material.

8. A laminate comprising the film according to claim 7.

9. A display device comprising the film according to claim 7.

* * * * *